US009862672B2

(12) United States Patent
Uhrich et al.

(10) Patent No.: US 9,862,672 B2
(45) Date of Patent: Jan. 9, 2018

(54) ANTIOXIDANT-BASED POLY(ANHYDRIDE-ESTERS)

(71) Applicant: RUTGERS, THE STATE UNIVERSITY OF NEW JERSEY, New Brunswick, NJ (US)

(72) Inventors: Kathryn Uhrich, New Brunswick, NJ (US); Michelle Morano, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 7 days.

(21) Appl. No.: 14/894,166

(22) PCT Filed: May 29, 2014

(86) PCT No.: PCT/US2014/039970
§ 371 (c)(1),
(2) Date: Nov. 25, 2015

(87) PCT Pub. No.: WO2014/194055
PCT Pub. Date: Dec. 4, 2014

(65) Prior Publication Data
US 2016/0130211 A1 May 12, 2016

Related U.S. Application Data

(60) Provisional application No. 61/828,534, filed on May 29, 2013.

(51) Int. Cl.
| | | |
|---|---|---|
| A61K 8/02 | (2006.01) |
| A61K 8/37 | (2006.01) |
| A61Q 17/04 | (2006.01) |
| C07C 69/734 | (2006.01) |
| C08G 63/06 | (2006.01) |
| C08G 63/66 | (2006.01) |

(52) U.S. Cl.
CPC ............ *C07C 69/734* (2013.01); *A61K 8/025* (2013.01); *A61K 8/37* (2013.01); *A61Q 17/04* (2013.01); *C08G 63/06* (2013.01); *C08G 63/66* (2013.01)

(58) Field of Classification Search
CPC .......... A61K 8/025; A61K 8/37; A61Q 17/04; C07C 69/734; C08G 63/06
See application file for complete search history.

(56) References Cited

U.S. PATENT DOCUMENTS

| | | |
|---|---|---|
| 2,607,799 A | 8/1952 | Weesner |
| 4,062,855 A | 12/1977 | Allan et al. |
| 4,126,445 A | 11/1978 | Allan et al. |
| 4,164,560 A | 8/1979 | Folkman et al. |
| 4,298,595 A | 11/1981 | Parkinson et al. |
| 4,375,968 A | 3/1983 | Manhart et al. |
| 4,414,203 A | 11/1983 | Cabardo, Jr. et al. |
| 4,559,157 A | 12/1985 | Smith |
| 4,591,496 A | 5/1986 | Cohen et al. |
| 4,608,392 A | 8/1986 | Jacquet |
| 4,612,302 A | 9/1986 | Szabo et al. |
| 4,684,620 A | 8/1987 | Hruby et al. |
| 4,757,128 A | 7/1988 | Domb et al. |
| 4,792,598 A | 12/1988 | Ziegast |
| 4,820,508 A | 4/1989 | Wortzman |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,938,949 A | 7/1990 | Borch et al. |
| 4,992,478 A | 2/1991 | Geria |
| 4,997,904 A | 3/1991 | Domb |
| 4,999,417 A | 3/1991 | Domb |

(Continued)

FOREIGN PATENT DOCUMENTS

| | | |
|---|---|---|
| AU | 750424 | 3/2003 |
| BR | PI 9400416-1 A | 8/1994 |

(Continued)

OTHER PUBLICATIONS

Aebischer, P., et al., "Basic fibroblast growth factor released from synthetic guidance channels facilitates peripheral nerve regeneration across long nerve gaps", *Journal of Neuroscience Research*, 23(3), 282-289, (Jul. 1989).
Anastasiou, T.J., "Novel, Degradable Polyanhydrides", *25th Annual Meeting Transactions of the Society for Biomaterials*, Abstract, 79, (1999).
Anastasiou, T.J., "Novel Polyanhydrides with Enhanced Thermal and Solubility Properties", *Macromolecules*, 33(17), 6217-6221, (2000).
Anastasiou, T.J., "Synthesis of Novel, Degradable Polyanhydrides Containing Para-Aminosalicylic Acid as Drug Delivery Devices for Tuberculosis Treatment", *Polymer Preprints*, 41(2), 1366-1367, (Aug. 2000).
Arredondo et al., Effects of Linkers Substitution on Salicylic Acid-derived Poly(anhydride-esters), website of Rutgers, the State University of New Jersey, 16 pages (2001).

(Continued)

*Primary Examiner* — Alma Pipic
(74) *Attorney, Agent, or Firm* — Viksnins Harris Padys Malen LLP

(57) ABSTRACT

Certain embodiments of the invention provide antioxidant-based diacids and polymers comprising glycol groups as described herein, and methods of use thereof. In certain embodiments the polymers described herein are formulated as microspheres or hydrogels. Described herein is the chemical incorporation of antioxidants, e.g., coumaric acid, ferulic acid, and sinapic acid, into a polymer backbone for use, e.g., in applications for localized release and rapid delivery. As provided, the chemical composition of the linker molecules used (of which hold together two bioactives via ester linkages) may be used to vary the hydrophilicity of the polymer. The bioactive release rate may also be altered for a tunable release delivery system, allowing for increased bioactive release compared to other linkers previously utilized.

19 Claims, 8 Drawing Sheets

(56) References Cited

U.S. PATENT DOCUMENTS

| | | |
|---|---|---|
| 5,032,216 A | 7/1991 | Felten |
| 5,082,925 A | 1/1992 | Shalaby et al. |
| 5,160,745 A | 11/1992 | DeLuca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 5,981,739 A | 11/1999 | Anderson et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 6,790,798 B1 | 9/2004 | Suzuki et al. |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,901,705 B2 | 3/2011 | Roby et al. |
| 7,985,415 B2 | 7/2011 | Giroux |
| 8,017,714 B2 | 9/2011 | Uhrich |
| 8,088,405 B2 | 1/2012 | Uhrich et al. |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 9,108,070 B2 | 8/2015 | Kanamathareddy et al. |
| 9,144,579 B2 | 9/2015 | Uhrich et al. |
| 9,387,250 B2 | 7/2016 | Uhrich et al. |
| 2001/0046476 A1 | 11/2001 | Polchocka |
| 2003/0035787 A1 | 2/2003 | Uhrich et al. |
| 2003/0059469 A1 | 3/2003 | Uhrich et al. |
| 2003/0082225 A1 | 5/2003 | Mason |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0048121 A1 | 3/2005 | East et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2006/0062768 A1 | 3/2006 | Hnojewyj |
| 2006/0115457 A1 | 6/2006 | Hnojewyj |
| 2007/0098800 A1 | 5/2007 | Giroux et al. |
| 2007/0196417 A1 | 8/2007 | Uhrich et al. |
| 2007/0213500 A1 | 9/2007 | Uhrich et al. |
| 2010/0152410 A1 | 6/2010 | East et al. |
| 2010/0272670 A1 | 10/2010 | Uhrich et al. |
| 2010/0291180 A1 | 11/2010 | Uhrich et al. |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2012/0058155 A1 | 3/2012 | Uhrich et al. |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |
| 2016/0058776 A1 | 3/2016 | Kanamathareddy et al. |
| 2016/0175343 A1 | 6/2016 | Uhrich et al. |

FOREIGN PATENT DOCUMENTS

| | | |
|---|---|---|
| CA | 2393676 | 7/2002 |
| DE | 288311 | 3/1991 |
| DE | 0288387 | 3/1991 |
| EP | 0107376 A1 | 5/1984 |
| EP | 0246341 | 11/1987 |
| EP | 0483429 | 5/1992 |
| EP | 0498283 | 8/1992 |
| EP | 0580386 | 1/1994 |
| EP | 0610056 A1 | 8/1994 |
| FR | 2839451 | 11/2003 |
| JP | 45004740 | 2/1970 |
| JP | 51-134729 | 11/1976 |
| JP | 53-082743 | 7/1978 |
| JP | 56-007716 | 1/1981 |
| JP | 6255797 | 12/1985 |
| JP | 61186309 | 8/1986 |
| JP | 06-328857 | 11/1994 |
| JP | 07-149044 | 6/1995 |
| NL | 9000237 | 8/1991 |
| NO | 2001030407 A1 | 5/2001 |
| WO | WO 90/09779 | 9/1990 |
| WO | WO 91/09831 | 7/1991 |
| WO | WO 91/18940 | 12/1991 |
| WO | WO 97/39738 | 10/1997 |
| WO | WO 97/44016 | 11/1997 |
| WO | WO 97/49385 | 12/1997 |
| WO | WO 98/36013 | 8/1998 |
| WO | WO 99/12990 | 3/1999 |
| WO | WO 99/29885 | 6/1999 |
| WO | WO 99/36107 | 7/1999 |
| WO | WO 00/66730 | 11/2000 |
| WO | WO 01/28492 | 4/2001 |
| WO | WO 01/41753 | 6/2001 |
| WO | WO 02/09767 | 2/2002 |
| WO | WO 02/09768 | 2/2002 |
| WO | WO 02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |

(56) References Cited

FOREIGN PATENT DOCUMENTS

| WO | WO 2008/128193 | 10/2008 |
|---|---|---|
| WO | WO 2009/026544 | 2/2009 |
| WO | WO 2012/139015 | 10/2012 |
| WO | WO 2014/194055 | 12/2014 |
| WO | WO 2015/191742 | 12/2015 |

OTHER PUBLICATIONS

Attawia, M.A., "Biocompatibility Testing of Poly(anhydride-co-imides) Containing Pyromellitylimidoalanine", *The 21st Annual Meeting of the Society for Biomaterials*, Abstract, 222, (Apr. 5-9, 1994).
Attawia, M.A., "Cytotoxicity testing ofpoly(anhydride-co-imides) for orthopedic applications", *Journal of Biomedical Materials Research*, 29(10), 1233-1240, (1995).
Attawia, M.A., "In vitro bone biocompatibility of poly(anhydride-co-imides) containing pyromellitylimidoalanine", *Journal of Orthopedic Research*, 14(3), 445-454, (1996).
Attawia, M.A., "The Long Term Osteoblast Response to Poly(anhydride-co-imides): A New Degradable Polymer for Use in Bone", *Proceedings of the Fifth World Biomaterials Congress*, Toronto, Canada, 113, (1996).
Attawia, M.A., "Proliferation, Morphology, and Protein Expression by Osteoblasts Cultured on Poly(anhydride-co-amides)", *Journal of Biomedical Materials Research*, 48(3), 322-327, (1999).
Attawia, M.A., "Regional drug delivery with radiation for the treatment of Ewing's sarcoma—in vitro development of a taxol release system", *Journal of Controlled Release*, 71, 193-202 (2001).
Beaton, M.L., "Synthesis of a novel poly(anhydride-ester)", *The Rutgers Scholar—An Electronic Bulletin of Undergraduate Research*, 3, 1-7, (2001), http://www.scils.rutgers.edu/~weyang/ejournal/volume03/beatuhri/beatuhri.htm.
Bedell, C., "Processing and Hydrolytic Degradation of Aromatic, Ortho-Substituted Polyanhydrides", *Journal of Applied Polymer Science*, 80, 32-38, (2001).
Brambley, D., et al., "Microlithography: an overview", *Advanced Materials for Optics and Electronics*, 4(2), 55-74, (Mar.-Apr. 1994).
Branch, D.W., "Microstamp patterns of biomolecules for high resolution neuronal networks", *Medical & Biological Engineering & Computing*, 36(1), 135-41, (Jan. 1998).
Brown, J.P., "A Polymeric Drug for Treatment of Inflammatory Bowel Disease", *Journal of Medicinal Chemistry*, 26(9), 1300-1307, (1983).
Brown, L., et al., "Transdermal delivery of drugs", *Annual Review of Medicine*, 39, 221-9, (1988).
Cai et al., "Salicylic acid and PEG-contained polyanhydrides: synthesis, characterization, and in vitro salicylic acid release", Drug Delivery 12 (2), 97-102 (2005).
Campo, C.J., "Polyanhydrides: the effects of ring substitution changes on polymer properties", *Polymer Bulletin*, 42, 61-68, (1999).
Carbone et al., "Design and Synthesis of Fast-Degrading Poly(anhydride-esters)", *Macromol. Rapid Commun.*, 30, 1021-1026 (2009).
Chafi, N., "Dosage Form with Salicylic Acid Attached to the Polyanhydride Polymer Dispersed in an Eudragit Matrix", *International Journal of Pharmaceutics*, 52, 203-211, (1989).
Chatterjee, R., et al., "Mechanism for the Increase in Solubility of Deoxyhemoglobin S due to Cross-Linking the Beta Chains Between Lysine-82 Beta1 and Lysine-82 Beta 2", *Biochemistry*, 21, 5901-5909, (1982).
Chen, G., "Effect of protein and cell behavior on pattern-grafted thermoresponsive polymer", *Journal of Biomedical Materials Research*, 42(1), 38-44, (Oct. 1998).
Conix, A., "New High-Melting Fibre-Forming Polymers", *Die Makromolekulare Chemie*, XXIV, 76-78, (1957).
Conix, A., "Aromatic Polyanhydrides, a New Class of High Melting Fiber-Forming Polymers", *Journal of Polymers Science*, XXIX, 343-353, (1958).

Conix, A., "Poly [1,3-bis (p carboxyphenoxy)—Propane anhydride]", *Macromolecular Synthesis*, 2, 95-99, (1996).
Cotlier, "Distribution of salicylate in lens and intraocular fluids and its effect on cataract formation", *American Journal of Medicine*, 74 (6A), 83-90 (1983).
Cotlier, "Senile Cataracts: Evidence for Acceleration by Diabetes and Deceleration by Salicytate", *Canadian Journal of Ophthalmology*, 16(3), 113-118 (1981).
Davaran, S., "Release of 5-amino Salicylic Acid from Acrylic Type Polymeric Prodrugs Designed for Colon-specific Drug Delivery", *Journal of Controlled Release*, 58(3), 279-287, (1999).
Davies, M.C., "The Analysis of the Surface Chemical Structure of Biomedical Aliphatic Polyanhydrides Using SPX and ToF-SIMS", *Journal of Applied Polymer Science*, 42, No. 6, New York, US, 1597-1605, (Mar. 20, 1991).
Delamarche, E., et al., "Patterned delivery of immunoglobulins to surfaces using microfluidic networks", *Science*, 276(5313), 779-781, (May 2, 1997).
Dewez, J.L., et al., "Adhesion of mammalian cells to polymer surfaces: from physical chemistry of surfaces to selective adhesion on defined patterns", *Biomaterials*, 19(16), 1441-1445, (Aug. 1998).
Domb, A.J., "Polyanhydrides. I. Preparation of High Molecular Weight Polyanhydrides", *Journal of Polymer Science: Part A: Polymer Chemistry*, 25, 3373-3386, (1987).
Domb, A.J., "Synthesis and Characterization of Biodegradable Aromatic Anhydride Copolymers", *Macromolecules*, 25, 12-17, (1992).
Dontha, N., "Generation of biotin/avidin/enzyme nanostructures with maskless photolithography", *Analytical Chemistry*, 69(14), 2619-25, (Jul. 15, 1997).
Dukovic, G., "Novel degradable poly(anhydride-esters) for controlled drug release", *The Rutgers Scholar—An Electronic Bulletin of Undergraduate Research*, 1, 1-10, (1999), http://www.scils.rutgers.edu/~weyang/ejournal/volume01/uhriduko/uhriduko.htm.
Erdmann, L., "Polymer Prodrugs with Pharmaceutically Active Degradation Products", *Polymer Preprints*, 38(2), 570-571, (1997).
Erdman et al., "Synthesis and Characterization of a Polymeric Prodrug", *Proceedings of the American Chemical Society Division of Polymeric Materials: Science and Engineering*, 78, Abstract Spring Meeting, Dallas, TX, pp. 194, (Apr. 1998).
Erdmann, L., et al., Chapter 5, "Polymeric Prodrugs: Novel Polymers with Bioactive Components", *In: Tailored Polymeric Materials for Controlled Delivery Systems*, I. McCulloh, et al., (Editors), ACS Symposium Series 709, Developed from a symposium sponsored by the Division of Polymer Chemistry at the 214th National Meeting of the American Chemical Society, Las Vegas, Nevada, Sep. 7-11, 1997, American Chemical Society: Washington, D.C., 83-91, (1998).
Erdmann, L., "Polymeric Prodrugs: Novel Polymers for Delivery of Salicylic Acid", *Annals of Biomedical Engineering*, 26 (Suppl. 1), Abstract No. PB.26, Annual Fall Meeting, S-124, (1998).
Erdmann, L., "Polymeric Salicylic Acid: In Vitro and In Vivo Degradation", *Polymer Preprints*, 39(2), 224-225, (1998).
Erdmann, L., "Degradable poly(anhydride ester) implants: effects of localized salicylic acid release on bone", *Biomaterials*, 21(24), 2507-2512, (2000).
Erdmann, L., "Synthesis and degradation characteristics of salicylic acid-derived poly(anhydride-esters)", *Biomaterials*, 21(19), 1941-1946, (Oct. 2000).
Giammona, G., "Polymeric Prodrugs alpha beta poly-hyroxyethyl-dl-aspartamide as macromolecular carrier for some non-steroidal anti-inflammatory agents", *Abstracts from Database BIOSIS Online, Biosciences Information Service*, Philadelphia, PA, Original Publication from the International Journal of Pharmaceutics (Amsterdam), 1 page (1989).
Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, 55-62, (1989).
Gopferich, "Mechanisms of polymer degradation and erosion", Biomaterials 17(2), 103-114 (1996).
Gopferich et al., "Polyanhydride degradation and erosion", Adv Drug Deliv Rev 54, 911-931 (2002).

(56) References Cited

OTHER PUBLICATIONS

Gouin, S., et al., "New Polyanhydrides Made from a Bile Acid Dimer and Sebacic Acid: Synthesis, Characterization and Degradation", *Macromolecules*, 33, 5379-5383, (2000).
Graf, "Antioxidant potential of ferulic acid", Free Radical Bio Med 13, 435-448 (1992).
Herbert, C.B., "Micropatterning gradients and controlling surface densities of photoactivatable biomolecules on self-assembled monolayers of oligo(ethylene glycol) alkanethiolates", *Chemistry & Biology*, 4(10), 731-7, (Oct. 1997).
Hou et al., "Synthesis and erosion properties of PEG-containing polyanhydrides", Macromol Biosci 7(5), 620-628 (2007).
Hu et al., "One-pot preparation of caffeic acid esters from 3, 4-dihydroxybenzaldehyde", Journal of Chemical Research vol. 2006 (9), 586-588 (2006).
Ibim, S., "Controlled Release Based on Poly(anhydride-co-imides)", *Proc. Intern. Symp. Control. Rel. Bioact. Mater.*, 22, 2 pgs, (1995).
Ibim, S.M., "Poly(anhydride-co-imides): In Vivo Biocompatibility in a rat model", *Biomaterials*, 19(10), 941-951, (1998).
Ibim, S.E., "Preliminary in vivo report on the osteocompatibility of poly(anhydride-co-imides) evaluated in a tibial model.", *Journal of Biomedical Material Research*, 43(4), 374-379, (Winter 1998).
Ito, Y., "Micropatterned immobilization of epidermal growth factor to regulate cell function", *Bioconjugate Chemistry*,9(2), 277-82, (Mar.-Apr. 1998).
James, C.D., "Patterned Protein Layers on Solid Substrates by Thin Stamp Microcontact Printing", *Langmuir*, 14(4), 741-744, (1998).
Jeffcoat, "The Effect of Systemic Flurbiprofen on Bone Supporting Dental Implants", *Journal of American Dental Associate*, 126, 305-311 (1995).
Jiang et al., "Preparation, characterization and degradation characteristics of polyanhydrides containing poly(ethylene glycol)", Polymer International vol. 48 (1), 47-52 (1999).
Jiang, H.L., "Synthesis, Characterization and In Vitro Degradation of a New Family of Alternate Poly(ester-anhydrides) Based on Aliphatic and Aromatic Diacids", *Biomaterials*, 22(3), 211-218, (2001).
Jucker, M., et al., "Fetal rat septals cells adhere to and extend processes on basement membrane, laminin, and a synthetic peptide from the laminin A chain sequence", *Journal of Neuroscience Research*, 28(4), 507-17, (Apr. 1991).
Kleinfeld, D., "Controlled outgrowth of dissociated neurons on patterned substrates", *Journal of Neuroscience*, 8(11), 4098-120, (Nov. 1998).
Kregel et al, "An integrated view of oxidative stress in aging: basic mechanisms, functional effects, and pathological considerations", Am J Physiol Regul Integr Comp Physiol 292(1), R18-36 (2007).
Krogh-Jespersen, E., "Synthesis of a Novel Aromatic Polyanhydride Containing Aminosalicylic Acid", *Polymer Preprints*, 41(1), 1048-1049, (2000).
Langer, R., "New Methods of Drug Delivery", *Science*, 249(4976), 1527-1533, (Sep. 1990).
Laurencin, C.T., "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, C.T., "Poly(anhydrides-co-imides): In Vivo Biocompatibility Study", *23rd Annual Meeting of the Society for Biomaterials*, New Orleans, LA, 483, (1997).
Laurencin, C.T., "The Biocompatibility of Poly(anhydride-co-imides): High Strength Polymers for Controlled Drug Delivery", *Proc. 24th Int'l Symp. Control. Rel. Bioact. Mater.*, 973-974, (1997).
Laurencin, et al., "The controlled delivery of radiosensitizers: taxol treatment for Ewing Sarcoma", *Proceedings of the 25th Int'l Symp. Control. Rel. Bioact. Mater.*, pp. 236-237, (1998).
Li et al., "In vitro controlled release of sodium ferulate from Compritol 888 ATO-based matrix tablets", Int J Pharm 324, 152-157 (2006).

Longer, M.A., "Sustained-Release Drug Delivery Systems", *Remington's Pharmaceutical Sciences*, 18th Edition, Chapter 91, 1676-1693, (1990).
Macedo, B., et al., "The in vivo Response to a Bioactive Biodegradable Polymer", *Journal of Dental Research*, 78, Abstract No. 2827, 459, (1999).
Macedo, B., "The In Vivo Response to Bioactive Polyanhydride Monofilament", *Journal of Dental Research*, 79 (Abstract No. 3872), 627, (2000).
March, Advanced organic chemistry: reactions, mechanisms, and structure, 4th Edition, New York: Willey, 419-437 (1992).
Meng et al., "Determination of the hydrophobicity of local anesthetic agents", Anal Biochem 292, 102-106 (2001).
Orrenius et al., "Mitochondrial oxidative stress: implications for cell death", Annu Rev Pharmacol Toxicol 47, 143-183 (2007).
Ouimet et al., "Bioactive-based Polymers: Applications for Skin Care", CRS Proc, Abstract #95, 2 pages, (Jul. 2013).
Ouimet et al., Synthesis, Characterization, and In Vitro Release Profiles of Biodegradable Hydroxycinnamate-based Poly(anhydride-esters), *PMSE Preprint*, 2 pages, (Aug. 2012).
Ouimet et al., Synthesis, Characterization, and In Vitro Release Profiles of Biodegradable Hydroxycinnamate-based Poly(anhydride-esters), Abstract No. 356, 244th ACS National Meeting & Exposition, Philadelphia, Pennsylvania, 1 page, (Jun. 2012).
Ouimet, Synthesis, Characterization, and In Vitro Release Profiles of Biodegradable Coumarate-based Poly(anhydride-esters), Presentation, 244th ACS National Meeting & Exposition, Aug. 19-23, 2012, Philadelphia, Pennsylvania, 24 pages, (Aug. 2012).
Ouimet et al., "Biodegradable Polymers with Naturally Derived Antioxidant and Antimicrobial Degradation Products", 5 pages, (poster), NYSCC Cosmetic Tech Transfer Conference, Nov. 2012.
Ouimet et al., "Biodegradable ferulic acid-containing poly(anhydride-ester): degradation products with controlled release and sustained antioxidant activity", Biomacromolecules 14(3), 854-861 (2013).
Ouimet et al., Biodegradable Coumaric Acid-Based Poly(anhydride-ester) Synthesis and Subsequent Controlled Release, Macromolecular Rapid Communications 34, 1231-1236 (2013).
Ouimet et al., "Ferulic Acid-Basd Polymers with Glycol Functionality as a Versatile Platform for Topical Applications", Biomacromolecules 16, 2911-2919 (2015).
Ouimet, "Design, synthesis, and fabrication of biodegradable, bioactive-based polymers for controlled release applications", Thesis Defense Presentation, Rutgers, the State University of New Jersey, 56 pages, (May 29, 2012).
Ouimet, "Design, synthesis, and fabrication of biodegradable, bioactive-based polymers for controlled release applications", Dissertation, Rutgers, the State University of New Jersey, 236 pages, (Oct. 2013).
Patent Cooperation Treaty, Search Report and Written Opinion for PCT/US2014/039970, 10 pages, Oct. 10, 2014.
Pinther, P., "Synthesis of Polyanhydrides Containing Ester Groups", *Die Makromolekulare Chemie, Rapid Communications*, 11(8), 403-408, (Aug. 1990).
Podda et al., "Low molecular weight antioxidants and their role in skin ageing", Clin Exp Dermatol 26, 578-582 (2001).
Prudencio, A., "Biodegradable Polyanhydrides for Controlled Drug Release", Dissertation submitted to the Graduate School—New Brunswick, Rutgers, The State University of New Jersey, 228 pages (Oct. 2006).
Prudencio, A., et al., "A Novel Approach for Incorporation of Mono-Functional Bioactive Phenols into Polyanhydrides", *Macromolecular Rapid Communications*, 30, 1101-1108, 2009.
Reynolds, et al., "Non-steroidal anti-inflammatory drug (NSAID)-derived poly(anhydride-esters) in bone and periodontal regeneration", *Current Drug Delivery*, 4(3), 233-239 (Jan. 1, 2007).
Schacht, E., "Polymers for Colon Specific Drug Delivery", *Journal of Controlled Release*, 39, 327-338, (1996).

(56) References Cited

OTHER PUBLICATIONS

Schmalenberg, K., "Microlithographic patterning of polymer substrates for directed neuronal", *Polymeric Materials Science Engineering*, 81, Fall Meeting, Aug. 22-26, 1999, New Orleans, LA., 97, (1999).
Schmalenberg, K., "Patterned Polymer Substrates for directing Neuronal Growth", *ACS Regional Mid-Atlantic Research Meeting*, (1999).
Schmalenberg, K., "Patterning of polymer substrates for directed neuronal growth studies", *Laboratory for Surface Modification*,(Mar. 18, 1999).
Schmalenberg, K., "Thin Stamp Microcontact Patterned Printing of Protein Layers on Polymer Substrates", *Transactions: Twenty-Fifth Annual Meeting of the Society for Biomaterials*, Apr. 28-May 2, 1999.
Schmeltzer et al., "Comparison of salicylate-based poly(anhydride-esters) formed via melt-condensation versus solution polymerization", J Biomater Sci Polym Ed 19, 1295-1306 (2008).
Seidel, J.O., "Erosion of Poly(anhydride-co-imides): A Preliminary Mechanistic Study", *J. Appl. Polym. Sci.*, 62(8), 1277-1283, (1996).
Shen, E., "Morphological Characterization of Erodible Polymer Carriers for Drug Release", *Proc. 26th Int'l Symp. Control. Rel. Bioact. Mater.*, 717-718, (1999).
Spargo, B.J., et al., "Spatially controlled adhesion, spreading, and differentiation of endothelial cells on self-assembled molecular monolayers", *Proceedings of the National Academy of Science USA*,91(23), 11070-11074, (Nov. 8, 1994).
Sparks, et al., "Life after Union: Polymers-R-Us", Presentation at Union College, 40 pages (2007).
St. John, P.M., "Diffraction-based cell detection using a microcontact printed antibody grating", *Analytical Chemistry*, 70(6), 1108-11, (Mar. 15, 1998).
Swinyard, "Pharmaceutical Necessities", *In: Remington's pharmaceutical sciences* by Joseph P. Remington;Alfonso R. Gennaro, Easton, PA.: Mack Pub. Co.: ISBN: 0912734043, 1286-1329 (1990).
Tashiro, K., et al., "A synthetic peptide containing the IKVAV sequence from the A chain of laminin mediates cell attachment, migration, and neurite outgrowth", *Journal of Biological Chemistry*, 264(27), 16174-82, (Sep. 25, 1989).
Torres et al., "Synthesis and characterization of novel polyanhydrides with tailored erosion mechanisms", J Biomed Mater Res Part A 76A, 102-110 (2006).
Uhrich, K.E., "Synthesis and Characterization of poly(anhydride co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA, 239-240, (1994).
Uhrich, K.E., "Synthesis and Characterization of Degradable poly(anhydride-co-imides)", *Macromolecules*, 28(7), 2184-2193, (1995).
Uhrich, K.E., "Degradation of poly(anhydride-co-imides): Novel Polymers for Orthopedic Applications", *Mat. Res. Soc. Symp. Proc.*, 394, 41-46, (1995).
Uhrich, K.E., "In Vitro Degradation Characteristics of Poly(anhydride-imides) Containing Pyromellitylimidoalanine", *J. Appl. Polymer Sci., Part A, Polym. Chem.*, 34(7) 1261-1269, (1996).
Uhrich, K.E., "In Vitro Degradation Characteristics of Poly(anhydride-imides) Containing trimellitylimidoglycine", *J. Appl. Polymer. Sci.*, 63(11), 1401-1411, (1997).
Uhrich, K.E., "Chemical Changes during in vivo degradation of poly(anhydride-imide) matrices", *Biomaterials*, 19(22), 2045-2050, (1998).
Uhrich, K.E., "Poly(anhydride-ester) Degradation: Mechanical Changes and Correlation to Antibiotic Release", *American Chemical Society, Abstracts of Papers, Part 2*, Abstract No. 121, 221$^{st}$ ACS National Meeting, San Diego, CA, Abstract 121, (2001).
Uhrich, K.E., "Synthesis of Aminosalicylate-based polyanhydride Prodrugs: Esters, Amides, and Azos", *American Chemical Society,*

*Abstracts of Papers, Part 2*, Abstract No. 407, 222nd ACS National Meeting, Chicago, IL, Abstract 407, (2001).
Uhrich, K.E., "Designing Polymers for Biomedical Applications", Presentation at Division of Engineering & Applied Science, Harvard University, Cambridge, MA, 50 pages (2002).
Vogel et al., "Synthesis of novel biodegradable polyanhydrides containing aromatic and glycol functionality for tailoring of hydrophilicity in controlled drug delivery devices", Biomaterials 26 (7), 721-728 (2005).
Vokurkova et al., "Reactive oxygen species, cell growth, cell cycle progression and vascular remodeling in hypertension", Future Cardiol 3, 53-63 (2007).
Wang et al., "Chemical stability and degradation mechanisms of ferulic acid (F.A) within various cosmetic formulations", J Cosmet Sci 62, 483-503 (2011).
Woo et al., "Synthesis and characterization of a novel biodegradable antimicrobial polymer", *Biomaterials*, 21, 1235-1246 (2000).
Woo, G.L., "Biological Characterization of a Novel Biodegradable Antimicrobial Polymer Synthesized with Fluoroquinolones", *J. Biomed. Mater. Res.* 59, 35-45, (2002).
Yazdi et al., "Effects of non-steroidal anti-inflammatory drugs on demineralized bone-induced bone formation", *Journal of Periodontal Research*, 27(1), 28-33, (Jan. 1992).
Yeagy, "Characterization and in vitro degradation of salicylate-derived poly(anhydride-ester) microspheres)", J Microencapsulation 23(6), 643-653 (2006).
Yoda, N., "Synthesis of polyanhydrides. XII. Crystalline and high melting polyamidepolyanhydride of methylenebis(p-carboxybhenyl)amide", *Journal of Polymer Science*, 1, 1323-1338, (1963).
Zaugg, R.H., et al., "Modification of Hemoglobin with Analogs of Aspirin", *The Journal of Biological Chemistry*, 255(7), 2816-2821, (1980).
Abd El-Mohdy, et al., "Biodegradability, antimicrobial activity and properties of PVA/PVP hydrogels prepared by y-irradiation", J. Polym. Res., 16, 1-10 (2009).
Barros, et al., "Poly(N-vinyl-2-pyrrolidone) hydrogels produced by Fenton reaction", Polymer, 47, 8414-8419 (2006).
Carbone, "Natural Bioactive-Based Polyanhydrides for Controlled Release Applications", PhD Dissertation, Rutgers, The State University of New Jersey, 206 pages (2009).
CDC, NIOSH, Pocket Guide to Chemical Hazards, Trimellitic anhydride, retrieved from Internet: http://www.cdc.gov/niosh/npg/npgd0635.thml, 2 pages, downloaded Nov. 24, 2013.
Costache, et al., "Polymer-xerogel composites for controlled release wound dressings", Biomaterials, 31(24), 6336-6343 (2010).
Fogaca, et al., "Bioactive-based Polyanhydride/PVP Physically Cross-linked Hydrogels", Polymer Drug Delivery Symposium, Rutgers University, Abstract and corresponding Poster, 2 pages (2010).
Fogaca, et al., "Synthesis and Characterization of Novel Bioactive PVP-based Hydrogels", 240th ACS National Meeting and Exposition, Boston, MA, Abstract #153 and corresponding poster, 2 pages (2010).
Fogaca, et al., "Synthesis and Characterization of Novel Bioactive PVP-based Hydrogels", ACS Div Polym Mater: Sci Eng Fall 2010, PMSE Preprints, vol. 103, 450-451 (2010).
Fukushima, (Examiner), Office Action issued by the Japanese Patent Office and English language summary, dispatched Nov. 30, 2010, 9 pages.
Hoare, et al., "Hydrogels in drug delivery: Progress and challenges", Polymer, 49(8), 1993-2007 (2008).
Lopergolo, et al., "Direct UV photocrosslinking of poly(N-Vinyl-2-pyrrolidone) (PVP) to produce hydrogels", Polymer, 44(20), 6217-6222 (2003).
Nagata, et al., "Biodegradable elastic photocured polyesters based on adipic acid, 4-hydroxycinnamic acid and poly (ε-caprolactone) diols", Polymer, 45(1), 87-93 (2004).
Nagata, et al., "Synthesis and Characterization of Photocrosslinkable Biodregradable Polymers Derived from 4-Hydroxycinnamic Acid", Macromolecular Bioscience, 3(8), 412-419 (2003).
Ou, et al., "Role of ferulic acid in preparing edible films from soy protein isolate", Journal of Food Eng., 70, 205-210 (2005).

(56) References Cited

OTHER PUBLICATIONS

Ouimet, et al., "Biodegradable salicylate-based poly(anhydride-ester)/polyvinylpyrrolidone blends as hydrogel drug Delivery systems", 243rd ACS National Meeting and Exposition, San Diego, CA, Abstract #185 and corresponding presentation, 29 pages (2012).

Ouimet, et al., "Biodegradable salicylate-based poly(anhydride-ester)/polyvinylpyrrolidone blends as hydrogel drug delivery systems", POLY Preprints 53(1), 548-549 (2012).

Peppas, et al., Chapter 1.2.5 Hydrogels, in B.D. Ratner et al., (Eds.), Biomaterials Science (Third Edition): An Introduction to Materials in Medicine, Amsterdam, Elsevier, 166-179 (2013).

Peppas, et al., "Physicochemical Foundations and Structural Design of Hydrogels in Medicine and Biology", Annu. Rev. Biomed. Eng., 2, 9-29 (2000).

Prudencio, et al., "Effect of Linker Structure on Salicylic Acid-Derived Poly(anhydride-esters)", Macromolecules 38, 6895-6901 (2005).

Rumore, et al., "Potential Role of Salicylates in Type 2 Diabetes", The Annals of Pharmacotherapy, vol. 44, 1207-1221 (2010).

Su, et al., "Anti-inflammatory peptide-functionalized hydrogels for insulin-secreting cell encapsulation", Biomaterial, 31(2), 308-314 (2010).

Trombino, et al., "Synthesis and antioxidant activity evaluation of a novel cellulose hydrogel containing trans-ferulic acid", Carbohydrate Polymers, 75, 184-188 (2009).

U.S. Office Action, Final, for U.S. Appl. No. 13/473,383, 16 pages, dated Nov. 17, 2015.

U.S. Office Action, Final, for U.S. Appl. No. 13/473,383, 25 pages, dated Jul. 31, 2014.

U.S. Office Action, Final, for U.S. Appl. No. 13/473,383, 27 pages, dated Oct. 31, 2014.

U.S. Office Action, Non-Final, for U.S. Appl. No. 13/473,383, 18 pages, dated Dec. 3, 2013.

U.S. Office Action, Non-Final, for U.S. Appl. No. 13/473,383, 13 pages, dated Mar. 28, 2017.

U.S. Office Action, Non-Final, for U.S. Appl. No. 13/473,383, 17 pages, dated Apr. 29, 2015.

U.S. Office Action, Non-Final, for U.S. Appl. No. 13/473,383, 19 pages, dated Jan. 14, 2014.

Zhang, et al., "Synthesis and Characterization of Biodegradable Hydrophobic-Hydrophilic Hydrogel Networks with a Controlled Swelling Property", Journal of Polymer Science Part A: Polymer Chemistry, 38(13), 2392-2404 (2000).

A.

B.

ANTIOXIDANT-BASED POLY(ANHYDRIDE-ESTERS)

CROSS-REFERENCE TO RELATED APPLICATION

This application is the U.S. National Phase under 35 U.S.C. 371 of International Application Number PCT/US2014/039970 filed on May 29, 2014, which claims the benefit under 35 U.S.C. §119(e) of U.S. Provisional Application No. 61/828,534 filed on May 29, 2013, the entire contents of which are hereby incorporated by reference.

GOVERNMENT FUNDING

This invention was made with government support under P200A120078 awarded by the Department of Education and under R01 DE013207 awarded by the National Institutes of Health. The government has certain rights in the invention.

BACKGROUND OF THE INVENTION

There is significant evidence demonstrating the role of antioxidants in protecting cells from free radical species. Free radicals have been identified as major sources of oxidative stress in cells leading to DNA damage. This increased oxidative stress has been implicated in various deleterious conditions including cardiovascular diseases, neurodegenerative diseases, and cancer, while also contributing to the physiology of ageing. The human body combats this oxidative stress by employing antioxidants made in the body or acquired from diet and/or supplements. These antioxidants, however, are usually not in sufficient levels to overcome the damage from oxidative stress accumulation. Therefore, there has been much effort in the development of topical antioxidants with photoprotective and therapeutic efficacy.

Ferulic acid is a hydroxycinnamic acid and potent ubiquitous plant antioxidant due to its phenolic and extended side chain conjugation, which forms a resonance-stabilized phenolic radical. Ferulic acid has been studied as an ultraviolet absorber for enhanced skin protection against photodamage and has been approved as a sunscreen in Japan. While ferulic acid can be quite useful, its limited elimination half-life (less than 2 hours) and stability issues (degradation over time) lower its efficacy in current formulations.

Accordingly, new antioxidant compositions (e.g., ferulic acid compositions) are needed.

SUMMARY OF THE INVENTION

Accordingly, certain embodiments of the invention provide a diacid or polymer as described herein.

Certain embodiments of the invention provide a microsphere comprising a polymer as described herein.

Certain embodiments of the invention provide a pharmaceutical composition comprising a diacid, polymer or microsphere as described herein and a pharmaceutically acceptable carrier.

Certain embodiments of the invention provide a cosmetic comprising a diacid, polymer or microsphere as described herein.

Certain embodiments of the invention provide a sunscreen comprising a diacid, polymer or microsphere as described herein.

Certain embodiments of the invention provide a method to reduce oxidative stress in a mammalian cell (e.g., a human cell), comprising administering a diacid, polymer or microsphere as described herein to the mammal.

Certain embodiments of the invention provide a method to prevent photodamage to a mammal's skin (e.g. human), comprising administering a diacid, polymer or microsphere as described herein to the mammal.

Certain embodiments of the invention provide a method to treat a disorder associated with oxidative stress in a mammal (e.g., human), comprising administering a diacid, polymer or microsphere as described herein to the mammal.

Certain embodiments of the invention provide a hydrogel comprising (a) a polymer as described herein; and (b) a hydrophilic polymer that is blended with the polymer of part (a).

Certain embodiments of the invention provide a method of making a hydrogel as described herein, comprising solvent casting (a) a polymer as described herein; and (b) a hydrophilic polymer; under conditions to provide a hydrogel.

Certain embodiments of the invention provide a method for promoting wound healing in a mammal, comprising contacting a hydrogel as described herein with a wound of the mammal.

Certain embodiments of the invention provide a method of therapeutically treating the skin of a mammal, comprising contacting a hydrogel as described herein with the skin of the mammal.

Certain embodiments of the invention provide a method of making a diacid, polymer, microsphere or hydrogel as described herein.

Certain embodiments of the invention provide a diacid, polymer, microsphere or hydrogel prepared by the methods described herein.

DETAILED DESCRIPTION

Figure 1:
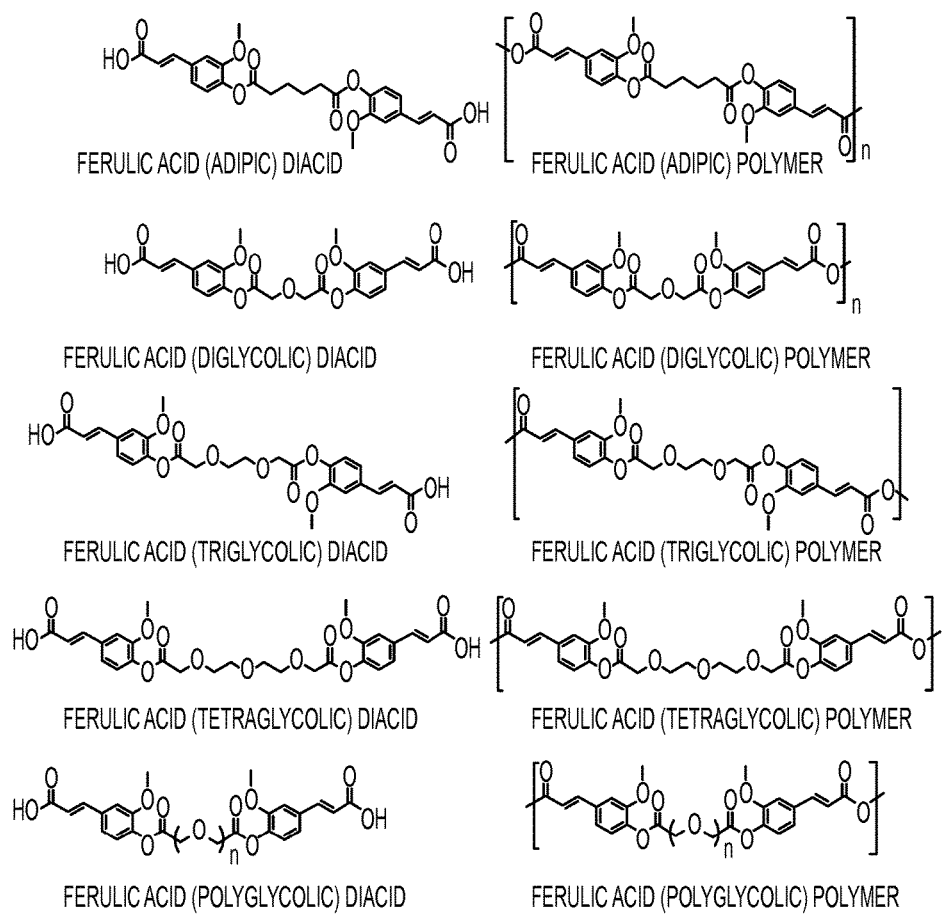
FIG. 1. Examples of ferulic acid-containing poly(anhydride-esters) and FA-containing diacids with various linker molecules.

Described herein is the chemical incorporation of antioxidants, e.g., coumaric acid, ferulic acid, and sinapic acid, into a polymer backbone for use, e.g., in applications for localized release and rapid delivery. As shown herein, the chemical composition of the linker molecules used (of which hold together two bioactives via ester linkages) may be used to vary the hydrophilicity of the polymer. The bioactive release rate may also be altered for a tunable release delivery system, allowing for increased bioactive release compared to other linkers previously utilized. Moreover, the polymer properties (thermal, mechanical, etc.) may also be tuned by altering the linker molecule. Overall, these tunable polymers may improve the quality, aesthetics, and performance of a product.

Accordingly, certain embodiments of the invention provide a diacid selected from:

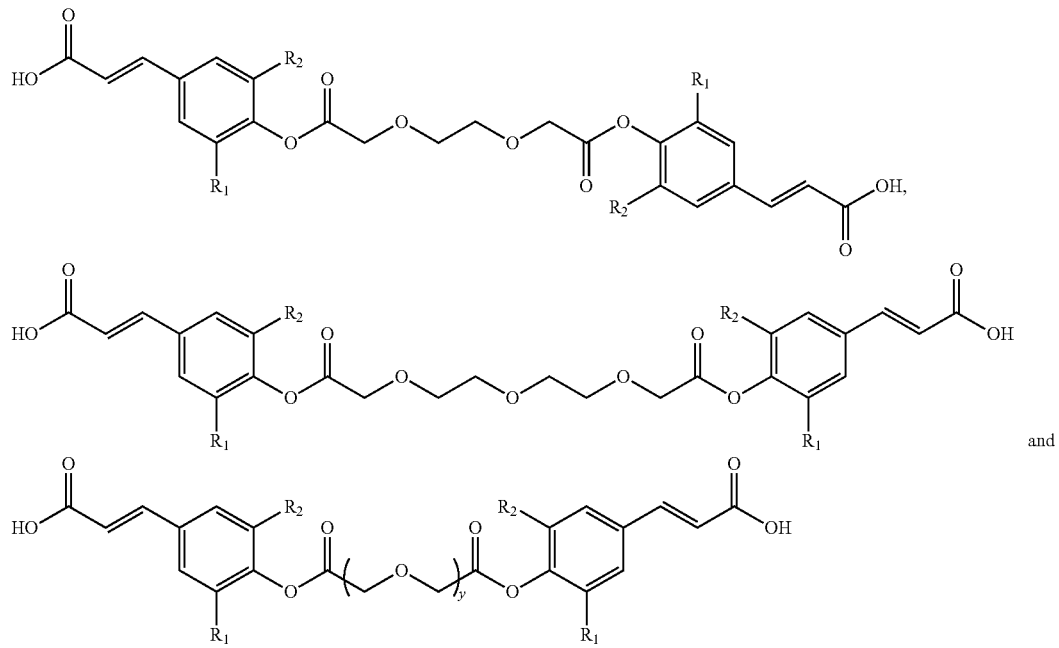

wherein $R_1$ is $OCH_3$ and $R_2$ is H; $R_1$ is $OCH_3$ and $R_2$ is $OCH_3$; or $R_1$ is H and $R_2$ is H; and
wherein y is 4 or more.

In certain embodiments, y is 5, 6, 7, 8, 9, 10, 11, 12, 13, 14, 15, 16, 17, 18, 19, 20, 21, 22, 23, 24, 25 or more.

In certain embodiments, $R_1$ is $OCH_3$ and $R_2$ is H.

In certain embodiments, $R_1$ is $OCH_3$ and $R_2$ is $OCH_3$.

In certain embodiments, $R_1$ is H and $R_2$ is H.

Certain embodiments of the invention provide a polymer selected from:

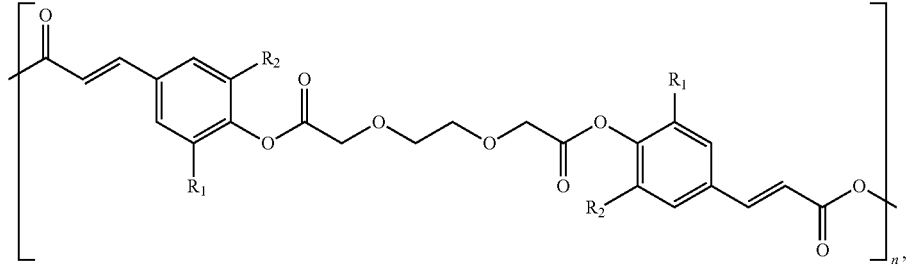

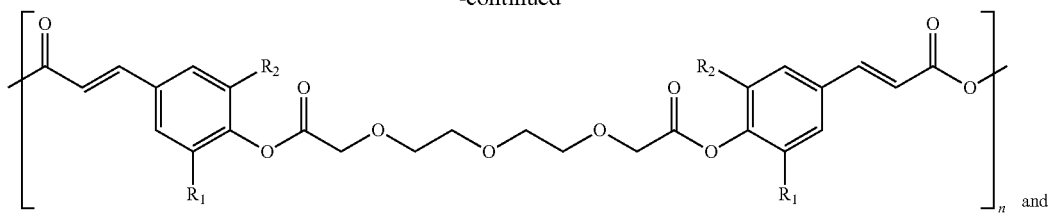

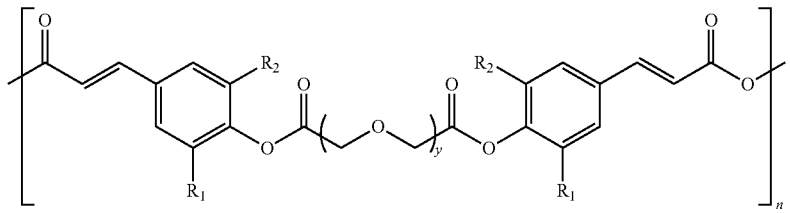

wherein $R_1$ is $OCH_3$ and $R_2$ is H; $R_1$ is $OCH_3$ and $R_2$ is $OCH_3$; or $R_1$ is H and $R_2$ is H;

wherein y is 4 or more;

and wherein n is 2 or more.

In certain embodiments, n is 3 or more. In certain embodiments, n is 4 or more. In certain embodiments, n is 5 or more. In certain embodiments, n is less than 2,000. In certain embodiments, n is less than 1,000. In certain embodiments, n is less than 500. In certain embodiments, n is less than 250. In certain embodiments, n is less than 150. In certain embodiments, n is less than 100. In certain embodiments, n is from about 5 to about 100. In certain embodiments, n is from about 5 to about 90. In certain embodiments, n is from about 5 to about 80. In certain embodiments, n is from about 5 to about 70. In certain embodiments, n is from about 5 to about 60. In certain embodiments, n is from about 10 to about 30. In certain embodiments, n is from about 10 to about 20. In certain embodiments, n is about 10.

In certain embodiments, y is 5, 6, 7, 8, 9, 10, 11, 12, 13, 14, 15, 16, 17, 18, 19, 20, 21, 22, 23, 24, 25 or more.

In certain embodiments, $R_1$ is $OCH_3$ and $R_2$ is H.

In certain embodiments, $R_1$ is $OCH_3$ and $R_2$ is $OCH_3$.

In certain embodiments, $R_1$ is H and $R_2$ is H.

In certain embodiments, the polymer has an average molecular weight of about 1,000 daltons to about 100,000 daltons. In certain embodiments, the polymer has an average molecular weight of about 5,000 daltons to about 100,000 daltons. In certain embodiments, the polymer has an average molecular weight of about 5,000 daltons to about 50,000 daltons. In certain embodiments, the polymer has an average molecular weight of about 10,000 daltons to about 30,000 daltons.

Certain embodiments of the invention provide a diacid as described herein.

Certain embodiments of the invention provide a polymer as described herein.

The polymers as described herein may be processed into microspheres using known methods and procedures commonly employed in the field of synthetic polymers, e.g., as described in the Examples.

Accordingly, certain embodiments of the invention provide a microsphere comprising a polymer as described herein.

Certain embodiments of the invention provide a microsphere comprising a polymer selected from:

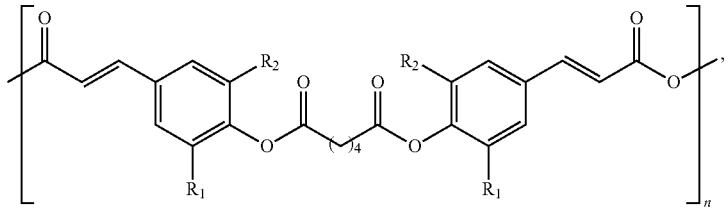

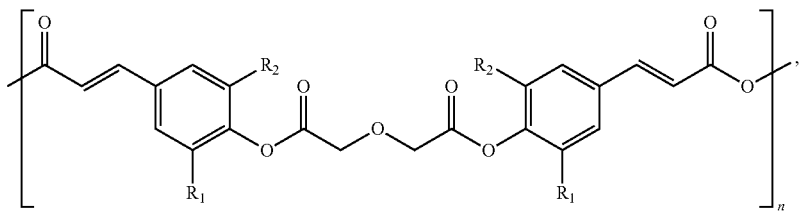

-continued

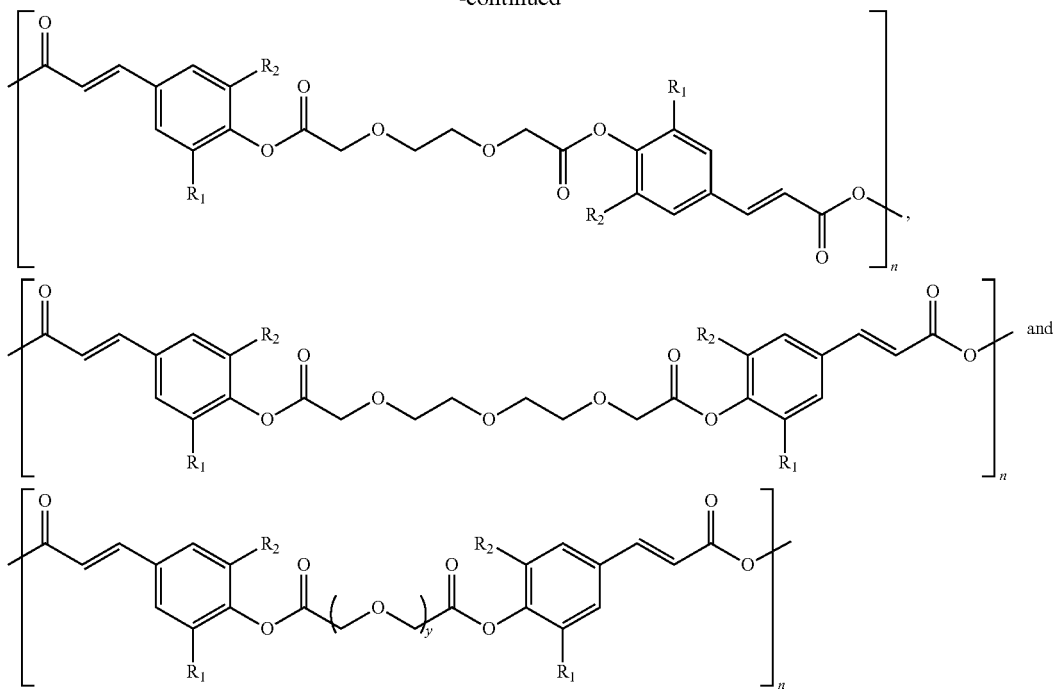

wherein $R_1$ is $OCH_3$ and $R_2$ is H; $R_1$ is $OCH_3$ and $R_2$ is $OCH_3$; or $R_1$ is H and $R_2$ is H;

wherein y is 4 or more;

and wherein n is 2 or more.

In certain embodiments, n is 3 or more. In certain embodiments, n is 4 or more. In certain embodiments, n is 5 or more. In certain embodiments, n is less than 2,000. In certain embodiments, n is less than 1,000. In certain embodiments, n is less than 500. In certain embodiments, n is less than 250. In certain embodiments, n is less than 150. In certain embodiments, n is less than 100. In certain embodiments, n is from about 5 to about 100. In certain embodiments, n is from about 5 to about 90. In certain embodiments, n is from about 5 to about 80. In certain embodiments, n is from about 5 to about 70. In certain embodiments, n is from about 5 to about 60. In certain embodiments, n is from about 10 to about 30. In certain embodiments, n is from about 10 to about 20. In certain embodiments, n is about 10.

In certain embodiments, y is 5, 6, 7, 8, 9, 10, 11, 12, 13, 14, 15, 16, 17, 18, 19, 20, 21, 22, 23, 24, 25 or more.

In certain embodiments, the diameter of the microsphere is between about 2 μm to about 100 μm. In certain embodiments, the diameter of the microsphere is between about 2 μm to about 90 μm. In certain embodiments, the diameter of the microsphere is between about 2 μm to about 80 μm. In certain embodiments, the diameter of the microsphere is between about 2 μm to about 70 μm. In certain embodiments, the diameter of the microsphere is between about 2 μm to about 60 μm. In certain embodiments, the diameter of the microsphere is between about 2 μm to about 50 μm. In certain embodiments, the diameter of the microsphere is between about 2 μm to about 40 μm. In certain embodiments, the diameter of the microsphere is between about 2 μm to about 30 μm.

Additional agents, synthetic or natural, may be incorporated in the microsphere described herein to achieve enhanced biological, mechanical, or other desired properties. Accordingly, in certain embodiments the microsphere comprises an additional agent(s) (e.g., the agent may be encapsulated by the microsphere). In certain embodiments, the additional agent(s) is a bioactive agent. For example, the additional bioactive agent may be encapsulated by the microspheres, resulting in a microsphere with a dual release of bioactive agents. In certain embodiments, the additional bioactive agent(s) is the same as the bioactive in the polymer backbone (e.g., ferulic acid, coumaric acid or sinapic acid). In certain embodiments, the additional bioactive agent(s) is different from the bioactive in the polymer backbone. In certain embodiments, the additional agent is an antioxidant, an antimicrobial, a sunscreen, a UV-absorber, a dye, a pigment or preservative.

Certain embodiments of the invention provide a composition comprising a diacid, polymer or microsphere as described herein and a carrier.

Certain embodiments of the invention provide a pharmaceutical composition comprising a diacid, polymer or microsphere as described herein and a pharmaceutically acceptable carrier.

Certain embodiments of the invention provide a cosmetic comprising a diacid, polymer or microsphere as described herein.

Certain embodiments of the invention provide a sunscreen comprising a diacid, polymer or microsphere as described herein.

Certain embodiments of the invention provide a method to reduce oxidative stress in a mammalian cell (e.g., a human cell), comprising administering a diacid, polymer or microsphere as described herein to the mammal. For example, the diacid, polymer or microsphere may be administered to the mammal by contacting the mammalian cell with the diacid, polymer or microsphere (e.g., through topical administration).

Oxidative stress is typically defined as the condition in which the sum of free radicals (i.e., reactive oxygen species)

within cells are greater than the antioxidant capacity of the cell, thus creating an imbalance. Disorders associated with oxidative stress are known to those skilled in the art, and include, e.g., cancer, such as skin cancer, as well as aspects related to the physiology of aging, neurodegenerative disorders such as Parkinson's disease, Alzheimer's disease, and amyotrophic lateral sclerosis, cardiovascular disorders such as atherosclerosis, cardiovascular disease, and hypertension, type II diabetes, age-related macular degeneration, osteoarthritis, and osteoporosis.

Certain embodiments of the invention provide a method to prevent photodamage to a mammal's skin (e.g. human), comprising administering a diacid, polymer or microsphere as described herein to the mammal. Photodamage to the skin is typically defined as the structural and functional deterioration of sun-exposed skin, resulting in wrinkling, roughness, altered texture, discoloration, acral lentigines, mottled hyperpigmentation, epidermal thickness, basophilic degeneration of dermis, collagen, dermal vessels, epithelial atypia, and/or dysplasia.

In certain embodiments, the diacid, polymer or microsphere is administered topically.

Certain embodiments of the invention provide a method to treat a disorder associated with oxidative stress in a mammal (e.g., human), comprising administering a diacid, polymer or microsphere as described herein to the mammal.

Certain embodiments of the invention provide a diacid, polymer or microsphere as described herein for use in medical treatment.

Certain embodiments of the invention provide the use of a diacid, polymer or microsphere as described herein to prepare a medicament useful for reducing oxidative stress in a mammalian cell (e.g., a human cell).

Certain embodiments of the invention provide the use of a diacid, polymer or microsphere as described herein to prepare a medicament useful for preventing photodamage to a mammal's skin.

Certain embodiments of the invention provide the use of a diacid, polymer or microsphere as described herein to prepare a medicament useful for treating a disorder associated with oxidative stress in a mammal.

Certain embodiments of the invention provide a diacid, polymer or microsphere as described herein for use in reducing oxidative stress.

Certain embodiments of the invention provide a diacid, polymer or microsphere as described herein for use in preventing photodamage to a mammal's skin.

Certain embodiments of the invention provide a diacid, polymer or microsphere as described herein for use in treating a disorder associated with oxidative stress in a mammal.

The polymers as described herein may be processed into hydrogels using known methods and procedures, e.g., as described in US Patent Publication US 2013/0022569, which is hereby incorporated by reference.

Accordingly, certain embodiments of the invention provide a hydrogel comprising a polymer as described herein. Typically, hydrogels are three-dimensional hydrophilic crosslinked polymer networks that can absorb large volumes of water and biological fluids without dissolving.

Certain embodiments of the invention provide a hydrogel comprising (a) a polymer as described herein; and (b) a hydrophilic polymer that is blended with the polymer of part (a).

In certain embodiments, the term "blend" may refer to crosslinking, wherein the hydrophilic polymer is crosslinked to the polymer described herein. As used herein, the term "crosslink" can refer to physical (e.g., intermolecular interactions or entanglements, such as through hydrophobic interactions) or chemical crosslinking (e.g., covalent bonding). Chemical crosslinking may be induced for these hydrogels using ultraviolet (UV) radiation, gamma radiation, an external cross-linking agent, or Fenton and photo-Fenton reactions to obtain chemical hydrogels. This chemical crosslinking may result in a more stable and non-reversible material, wherein the polymer described herein is trapped within the three-dimensional network of the hydrophilic polymer.

Accordingly, in certain embodiments, the polymer as described herein is physically crosslinked with the hydrophilic polymer through hydrophobic interactions.

In certain embodiments, the polymer described herein is chemically crosslinked with the hydrophilic polymer.

In certain embodiments, the polymer described herein is covalently crosslinked with the hydrophilic polymer.

In certain embodiments, the polymer described herein is crosslinked with the hydrophilic polymer using a free radical mechanism.

In certain embodiments, the ratio of the polymer as described herein and the hydrophilic polymer ranges between about 1:9 to about 1:1.

In certain embodiments, the ratio of the polymer described herein to the hydrophilic polymer ranges between about 1:9 to about 4:6. In certain embodiments, the ratio of the polymer described herein to the hydrophilic polymer ranges between about 1:9 to about 3:7. In certain embodiments, the ratio of the polymer described herein to the hydrophilic polymer ranges between about 1:9 to about 2:8. In certain embodiments, the ratio of the polymer described herein to the hydrophilic polymer is about 1:9. In certain embodiments, the ratio of the polymer described herein to the hydrophilic polymer is about 2:8. In certain embodiments, the ratio of the polymer described herein to the hydrophilic polymer is about 3:7. In certain embodiments, the ratio of the polymer described herein to the hydrophilic polymer is about 4:6. In certain embodiments, the ratio of the polymer described herein to the hydrophilic polymer is about 1:1.

As used herein, a "hydrophilic polymer" is a water-soluble polymer.

In certain embodiments, hydrophilic polymers capable of producing physical or chemical crosslinking in general with the polymers described herein may be used (e.g., polyvinylpyrrolidone (PVP), poly(vinyl alcohol) (PVA), polyurethane (PU) or poly(ethylene oxide)(PEO)).

Accordingly, in certain embodiments, the hydrophilic polymer comprises poly(N-vinyl-2-pyrrolidone), poly(vinyl alcohol), polyurethane or poly(ethylene oxide).

In certain embodiments, the hydrophilic polymer is poly(N-vinyl-2-pyrrolidone).

In certain embodiments, the hydrophilic polymer is a copolymer or blend of two or more polymers.

In certain embodiments, the two or more polymers are selected from poly(N-vinyl-2-pyrrolidone), poly(vinyl alcohol), polyurethane and poly(ethylene oxide).

In certain embodiments, the hydrophilic polymer as described herein has an average molecular weight of about 40,000 daltons to about 2,000,000 daltons. In certain embodiments, the hydrophilic polymer as described herein has an average molecular weight of about 100,000 daltons to about 2,000,000 daltons. In certain embodiments, the hydrophilic polymer as described herein has an average molecular weight of about 500,000 daltons to about 2,000,000 daltons. In certain embodiments, the hydrophilic polymer as described herein has an average molecular weight of about 750,000 daltons to about 2,000,000 daltons. In certain embodiments, the hydrophilic polymer as described herein has an average molecular weight of about 1,000,000 daltons to about 2,000,000 daltons. In certain embodiments, the hydrophilic polymer as described herein has an average molecular weight of about 1,000,000 daltons to about 1,750,000 daltons. In certain embodiments, the hydrophilic polymer as described herein has an average molecular weight of about 1,000,000 daltons to about 1,500,000 daltons. In certain embodiments, the hydrophilic polymer as described herein has an average molecular weight of about 1,300,000 daltons.

Additional bioactive molecules, synthetic or natural, may be incorporated in the hydrogels described herein to achieve enhanced biological or mechanical properties. For example, free bioactive molecules (e.g., curcumin) may be incorporated into the blended solution for hydrogel production, resulting in a material with dual release of bioactive molecules.

Accordingly, in certain embodiments, the hydrogel further comprises a bioactive molecule dispersed in the hydrogel.

In certain embodiments, the bioactive molecule dispersed in the hydrogel is the same as the bioactive molecule yielded by hydrolysis of the polymer backbone.

In certain embodiments, the bioactive molecule dispersed in the hydrogel is different from the bioactive molecule yielded by hydrolysis of the polymer backbone.

In certain embodiments, the bioactive molecule dispersed in the hydrogel is selected from ferulic acid, sinapic acid, coumaric acid (e.g., p-coumaric acid), salicylic acid and curcumin.

In certain embodiments the bioactive molecule dispersed in the hydrogel is curcumin.

As described herein, the synthesis of the hydrogels (e.g., the bioactive-based PVP/polyanhydride blended materials), may be prepared as films by solvent-cast methods. As described herein, the materials may be produced at varying ratios to achieve the desired formulation.

Certain embodiments of the invention provide a method of making a hydrogel as described herein, comprising solvent casting (a) a polymer as described herein; and (b) a hydrophilic polymer; under conditions to provide a hydrogel.

In certain embodiments, the solvent is DMF. In certain embodiments, the solvent is DMSO.

Certain embodiments further comprise cross-linking the polymer as described herein with the hydrophilic polymer using ultraviolet radiation, gamma radiation or an external cross-linking agent.

Certain embodiments of the invention provide a method for promoting wound healing in a mammal, comprising contacting a hydrogel as described herein with a wound (e.g., a burn) of the mammal (e.g., a human).

Certain embodiments of the invention provide a method of therapeutically treating the skin of a mammal, comprising contacting a hydrogel as described herein with the skin of the mammal (e.g., a human).

Certain embodiments of the invention provide the use of a hydrogel as described herein to prepare a medicament useful for promoting wound healing in a mammal.

Certain embodiments of the invention provide the use of a hydrogel as described herein to prepare a medicament useful for therapeutically treating the skin of a mammal.

Certain embodiments of the invention provide a hydrogel as described herein for use in promoting wound healing in a mammal.

Certain embodiments of the invention provide a hydrogel as described herein for use in therapeutically treating the skin of a mammal.

Certain embodiments of the invention provide a hydrogel as described herein for use in therapy.

Certain embodiments provide a hydrogel as described herein.

Certain embodiments of the invention provide a method of making a diacid, polymer, microsphere or hydrogel as described herein.

Certain embodiments of the invention provide a diacid, polymer, microsphere or hydrogel prepared by the methods described herein.

The invention also provides processes and intermediates disclosed herein that are useful for preparing diacids, polymers, microspheres and hydrogels described herein.

As used herein, the terms "treat" and "treatment" can refer to therapeutic treatment or to prophylactic or preventative treatment, wherein the object is to prevent or decrease an undesired physiological change or disorder, such as disorders associated with oxidative stress (e.g., cancer (e.g., skin cancer) or the physiology of aging).

The polymers and diacids of the invention can be formulated as compositions, e.g., pharmaceutical compositions, cosmetics and sunscreens, and administered to a mammalian host, such as a human patient in a variety of forms adapted to the chosen route of administration, e.g., orally or parenterally, by intravenous, intramuscular, topical or subcutaneous routes.

Thus, the present polymers and diacids may be systemically administered. Such compositions and preparations should contain at least 0.1% of the polymers or diacids. The percentage of the compositions and preparations may, of course, be varied and may conveniently be between about 2 to about 90% of the weight of a given unit dosage form. The amount of the polymers or diacids in such therapeutically useful compositions is such that an effective dosage level will be obtained.

For topical administration, the present polymers or diacids may be applied in pure form, e.g., when they are liquids, or may be applied as solutions. It will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the polymers or diacids can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The polymers can be formatted into microspheres, using known emulsion methods, or formatted into gels, using known hydrophilic polymers. The microspheres can be dispersed within creams, pastes, oils and the like for topical administration. Similarly, the polymers can be blended into gels with known hydrophilic polymers for topical administration.

Examples of useful dermatological compositions which can be used to deliver the present polymers to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of polymers and diacids of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the polymers or diacids of the invention, required for use in treatment will vary with the route of administration, the nature of the condition being treated and the age and condition of the patient and will be ultimately at the discretion of the attendant physician or clinician.

Certain embodiments of the invention will now be illustrated by the following non-limiting Examples.

Example 1

Ferulic Acid-Containing Polymers with Glycol Functionality for Tailoring Physicochemical Properties and Release Profiles.

The synthesis of a series of ferulic acid-containing polymers with aliphatic linkages have been achieved via solution polymerization methods. These compounds feature slower release rates than that desired for topical applications. Therefore, there is a need for a more rapid release rate for use in skin care formulations. To demonstrate this, a series of ferulic acid-containing polymers with ethylene glycol linkages were synthesized via solution polymerization methods. The polymers were characterized using nuclear magnetic resonance and Fourier transform infrared spectroscopies. The molecular weights and thermal properties were also determined. The glass transition temperatures and contact angles were obtained and the polymers compared. The polymer chemical structures and physical properties were shown to impact the release rates and antioxidant activity as drug delivery systems demonstrating the ability to strategically select polymers for various applications.

Introduction

Currently, there is significant evidence demonstrating the role of antioxidants in protecting cells from free radical species. Free radicals have been identified as major sources of oxidative stress in cells leading to DNA damage (Orrenius et al., *Annu Rev Pharmacol Toxicol* 2007, 47, 143-83). This increased oxidative stress has been implicated in various deleterious conditions including cardiovascular diseases, neurodegenerative diseases, and cancer (Vokurkova et al., *Future Cardiol* 2007, 3, 53-63), while also contributing to the physiology of ageing (Kregel K C, Zhang H J, *AJP: Regulatory, Integrative and Comparative Physiology* 2006, 292, R18-R36). The human body combats this oxidative stress by employing antioxidants made in the body or acquired from diet and/or supplements (Podda M, Grundmann-Kollmann M, *Clin Exp Dermatol* 2001, 26, 578-82; Kohen R, Gati I, *Toxicology* 2000, 148, 149-57). These antioxidants, however, are usually not in sufficient levels to overcome the damage from oxidative stress accumulation.

Therefore, there has been much effort in the development of topical antioxidants with photoprotective and therapeutic efficacy.

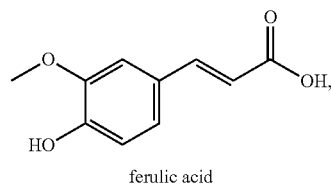

ferulic acid

Compound 1. Chemical Structure of the Bioactive Ferulic Acid with Many Beneficial Properties.

Ferulic acid is a hydroxycinnamic acid and potent ubiquitous plant antioxidant due to its phenolic and extended side chain conjugation, which forms a resonance stabilized phenolic radical (Graf E, *Free Radical Bio Med* 1992, 13, 435-48). Ferulic acid has been studied as an ultra-violet absorber for enhanced skin protection against photodamage and has been approved as a sunscreen in Japan. While ferulic acid can be quite useful, its limited elimination half-life (less than 2 hours) (Li et al., *Int J Pharm* 2006, 324, 152-7) and stability issues (degradation over time) lower its efficacy in current formulations (Wang et al., *J Cosmet Sci* 2011, 62, 483-503). Ferulic acid delivery can thus be improved by incorporation into a biodegradable polymer backbone (Ouimet et al., *Biomacromolecules* 2013, 14, 854-61), enabling controlled bioactive release and preventing active functional groups from degradation (Wang et al., *J Cosmet Sci* 2011, 62, 483-503; Ouimet et al., *Biomacromolecules* 2013, 14, 854-61). In this previously designed polymer, ferulic acid was stabilized (i.e., degradation and discoloration did not occur) and antioxidant activity was comparable to that of the free bioactive, indicating ferulic acid maintained its bioactivity over time (Ouimet et al., *Biomacromolecules* 2013, 14, 854-61).

Although this polymer demonstrated that ferulic acid could be stabilized via covalent incorporation into a polymer backbone, limited amounts of ferulic acid were released upon polymer degradation over the timeframe studied. For applications where a larger amount of ferulic acid is needed, increased drug release must be attained. A means to thus increase polymer degrade rates is to incorporate ethylene glycol functionalities into the polymer via copolymerization with poly(ethylene glycol) (PEG) or to incorporate ethylene glycol groups within the monomer unit. As described herein, ethylene glycol groups were employed as the linker molecule between two ferulic acid molecules allowing for increased hydrophilicity and tuning polymer physicochemical properties.

The development of tunable ferulic acid-containing biodegradable polymers by introducing ethylene glycol functionality as a linker molecule is described herein. By incorporating glycol groups into the polymer backbone, increased degradation rates were hypothesized. The synthesis, characterization, and drug release profiles of the glycol-modified polymers are discussed below.

Materials and Methods

Materials.

1 N hydrochloric acid (HCl), poly(vinylidine fluoride) and poly(tetrafluoroethylene) syringe filters, and Wheaton glass scintillation vials were purchased from Fisher Scientific (Fair Lawn, N.J.). All other reagents, solvents, and fine chemicals were purchased from Aldrich (Milwaukee, Wis.) and used as received.

$^1$H and $^{13}$C NMR and FT-IR spectroscopies.

$^1$H and $^{13}$C NMR spectra were recorded on a Varian 400 MHz or 500 MHz spectrometer using deuterated chloroform (CDCl$_3$) with TMS as internal reference or deuterated dimethyl sulfoxide (DMSO-d$_6$) as solvent and internal reference. FT-IR spectra were obtained using a Thermo Nicolet/Avatar 360 spectrometer, samples (1 wt %) ground and pressed with KBr into a disc. Each spectrum was an average of 32 scans.

Molecular Weight.

Polymer precursors were analyzed via mass spectrometry to determine molecular weights. A Finnigan LCQ-DUO equipped with Xcalibur software and an adjustable atmospheric pressure ionization electrospray ion source (API-ESI Ion Source) was used with a pressure of $0.8 \times 10^{-5}$ and 150° C. API temperature. Samples dissolved in methanol (<10 µg/mL) were injected with a glass syringe. GPC was used to determine polymer weight-averaged molecular weight and polydispersity using a Perkin-Elmer liquid chromatography system consisting of a Series 200 refractive index detector, a Series 200 LC pump, and an ISS 200 autosampler. Automation of the samples and processing the data was performed using a Dell OptiPlex GX110 computer running Perkin-Elmer TurboChrom 4 software with a Perkin-Elmer Nelson 900 Series Interface and 600 Series Link. Polymer samples were prepared for autoinjection by dissolving in dichloromethane (DCM, 10 mg/mL) and filtering through 0.45 µm poly(tetrafluoroethylene) syringe filters. Samples were resolved on a Jordi divinylbenzene mixed-bed GPC column (7.8×300 mm, Alltech Associates, Deerfield, Ill.) at 25° C., with DCM as the mobile phase at a flow rate of 1.0 mL/min. Molecular weights were calibrated relative to broad polystyrene standards (Polymer Source Inc., Dorval, Canada).

Thermal Properties.

DSC measurements were carried out on TA Instrument Q200 to determine melting ($T_m$) and glass transition ($T_g$) temperatures. Measurements on samples (4-6 mg) heated under nitrogen atmosphere from −10° C. to 200° C. at a heating rate of 10° C./min and cooled to −10° C. at a rate of 10° C./min with a two-cycle minimum were performed. TA Instruments Universal Analysis 2000 software, version 4.5A was used to analyze the data. TGA was utilized for determining decomposition temperatures ($T_d$) using a Perkin-Elmer Pyris 1 system with TAC 7/DX instrument controller and Perkin-Elmer Pyris software for data collection. Samples (5-10 mg) were heated under nitrogen atmosphere from 25° C. to 400° C. at a heating rate of 10° C./min. Decomposition temperatures were measured at the onset of thermal decomposition.

t-Butyl FA (2) Synthesis.

This was prepared according to previously published methods (see, FIG. 2, 2) (Ouimet et al., *Biomacromolecules* 2013, 14, 854-61; Hu et al., *J Chem Res-S* 2006, 586-8).

t-Butyl FA-Containing Diester Intermediate (3) Synthesis.

t-Butyl FA (2) (2 eq) was dissolved in anhydrous dimethylformamide (DMF) to which sodium hydride (NaH, 2.2 eq) was added slowly. After 30 minutes, acyl chloride (1 eq) dissolved in 10 mL DMF was added drop-wise at 20 mL/hr. Reaction progress was monitored by thin layer chromatography (5:1 hexane:ethyl acetate as eluent). Once completed, the reaction mixture was diluted with ethyl acetate (250 mL) and washed with deionized water (2×100 mL). The organic layer was collected, dried over MgSO$_4$, and the solvents removed in vacuo. This was purified on silica gel via flash chromatography using 5:1 hexane:ethyl acetate as eluent.

t-Butyl FA-Containing (Diglycolic) Diester Intermediate (3b).

Diglycolyl chloride (1 eq) was used as the acyl chloride. Yield: 72% (white powder). $^1$H-NMR (400 MHz, CDCl$_3$): δ 7.56 (d, 2H, J=16.0 Hz, R—CH═CH—R), 7.10 (s, 2H, Ar—H), 7.09 (d, 2H, Ar—H), 7.08 (d, 2H, Ar—H), 6.34 (d, 2H, J=16.0 Hz, R—CH═CH—R), 4.62 (s, 4H, CH$_2$), 3.86 (s, 6H, OCH$_3$), 1.54 (s, 18H, 3CH$_3$). $^{13}$C-NMR (CDCl$_3$): δ 167.9, 166.3, 151.3, 142.8, 140.7, 134.3, 123.2, 121.4, 120.9, 111.3, 80.9, 68.1, 56.2, 28.4. $T_m$: 222-223° C.

t-Butyl FA-Containing (Tetraglycolic) Diester Intermediate (3c).

To prepare the acyl chloride, 3,6,9-trioxaundecanedioic acid, termed tetraglycolic acid, (1 eq) was reacted neat in thionyl chloride (8 eq) and heated to reflux for 24 hours to yield a yellow liquid, termed tetraglycolyl dichloride. Tetraglycolyl dichloride (1 eq) was used directly as the acyl chloride. $^1$H-NMR (400 MHz, CDCl$_3$): δ 7.55 (d, 2H, J=16.0 Hz, R—CH═CH—R), 7.10 (s, 2H, Ar—H), 7.08 (d, 2H, Ar—H), 7.06 (d, 2H, Ar—H), 6.32 (d, 2H, J=16.0 Hz, R—CH═CH—R), 4.45 (s, 4H, CH$_2$), 3.84 (s, 6H, OCH$_3$), 3.78 (t, 4H, CH$_2$), 3.76 (t, 4H, CH$_2$), 1.54 (s, 18H, 3CH$_3$). $^{13}$C-NMR (CDCl$_3$): δ 168.6, 166.3, 151.4, 142.9, 141.2, 134.1, 123.2, 121.3, 120.8, 111.3, 80.9, 71.2, 70.9, 68.6, 56.1, 28.4. $T_m$: 239-242° C.

FA-Containing Diacid (4) Synthesis.

Compound 3 (1 eq) was dissolved in anhydrous DCM to which trifluoroacetic acid (TFA) (40 eq) was added and left to stir over-night. Solvent was removed in vacuo and the residue was triturated with DI water (300 mL), isolated via vacuum filtration, and dried in vacuo for 24 hours.

FA-Containing (Diglycolic) Diacid (4b).

Yield: 84% (white powder). $^1$H-NMR (500 MHz, DMSO-d$_6$): δ 12.43 (s, 2H, COOH), 7.58 (d, 2H, J=16.0 Hz, R—CH═CH—R), 7.51 (s, 2H, Ar—H), 7.29 (d, 2H, Ar—H), 7.20 (d, 2H, Ar—H), 6.60 (d, 2H, J=16.0 Hz, R—CH═CH—R), 4.60 (s, 4H, CH$_2$), 3.84 (s, 6H, OCH$_3$). $^{13}$C-NMR (DMSO-d$_6$): δ 171.6, 168.3, 151.8, 144.0, 141.5, 133.9, 123.8, 122.1, 120.2, 112.5, 56.6, 33.5, 24.4. IR (KBr, cm$^{-1}$): 3000-2500 (OH, COOH), 1752 (C═O, ester), 1696 (C═O, COOH), 1633 and 1600 (C═C). $T_m$: 241-244° C. ESI-MS m/z: 485 z−1.

FA-Containing (Tetraglycolic) Diacid (4c).

Yield: 98% (white crystals). $^1$H-NMR (500 MHz, DMSO-d$_6$): δ 12.40 (s, 2H, COOH), 7.51 (d, 2H, J=16.0 Hz, R—CH═CH—R), 7.41 (s, 2H, Ar—H), 7.18 (d, 2H, Ar—H), 7.08 (d, 2H, Ar—H), 6.52 (d, 2H, J=16.0 Hz, R—CH═CH—R), 4.35 (s, 4H, CH$_2$), 3.74 (s, 6H, OCH$_3$), 3.62 (t, 4H, CH$_2$), 3.54 (t, 4H, CH$_2$). $^{13}$C-NMR (DMSO-d$_6$): δ 169.0, 168.3, 151.7, 144.0, 140.9, 134.2, 123.8, 122.1, 120.4, 112.7, 70.8, 70.3, 68.1, 56.8. IR (KBr, cm$^{-1}$): 2920 (OH, COOH), 1780 (C═O, ester), 1690 (C═O, COOH), 1630 and 1600 (C═C). $T_m$: 86-89° C. ESI-MS m/z: 597 [z+Na]

FA-Containing Polymer (5) Synthesis.

Polymer (5) was prepared using a modified version of a previously described procedure (FIG. 2) (Schmeltzer et al., *J Biomater Sci Polym Ed* 2008, 19, 1295-306). Diacid 4 (1 eq) was dissolved in 20 mL anhydrous DCM under argon. After adding triethylamine (NEt$_3$, 4.4 eq), the reaction mixture was cooled to 0° C. Triphosgene (0.33 eq) dissolved in 10 mL anhydrous DCM was added drop-wise (20 mL/h). The reaction was allowed to stir at 0° C. until CO$_2$ evolution ceased (ca. 6 h). The reaction mixture was poured over chilled diethyl ether (400 mL) and the precipitate was isolated via vacuum filtration. The residue was dissolved in anhydrous DCM, washed with acidic water (1×250 mL), dried over MgSO$_4$, concentrated, and precipitated with an excess of chilled diethyl ether (500 mL) Ether was filtered off via vacuum filtration and polymer dried in vacuo at room temperature.

FA-Containing (Diglycolic) Polymer (5b).

Yield: 84% (white powder). $^1$H-NMR (500 MHz, DMSO-d$_6$): 7.93 (d, 2H, J=16.0 Hz, R—CH═CH—R), 7.66 (s, 2H, Ar—H), 7.45 (d, 2H, Ar—H), 7.28 (d, 2H, Ar—H), 6.94 (d, 2H, J=16.0 Hz, R—CH═CH—R), 4.63 (s, 4H, CH$_2$), 3.86 (s, 6H, OCH$_3$). $^{13}$C-NMR (DMSO-d$_6$): δ 168.3, 163.4, 151.8, 148.7, 141.8, 133.6, 124.0, 123.2, 118.0, 113.4, 67.9, 56.9. IR (KBr, cm$^{-1}$): 1780-1710 (C═O, anhydride and ester region), 1630 and 1600 (C═C). M$_w$=18,300 Da, PDI=1.3. T$_g$=108° C. T$_d$=338° C.

FA-Containing (Tetraglycolic) Polymer (5c).

Yield: 90% (light beige powder). $^1$H-NMR (500 MHz, DMSO-d$_6$): 7.87 (b, 2H, J=16.0 Hz, R—CH═CH—R), 7.58 (b, 2H, Ar—H), 7.38 (b, 2H, Ar—H), 7.20 (b, 2H, Ar—H), 6.86 (b, 2H, J=16.0 Hz, R—CH═CH—R), 4.42 (b, 4H, CH$_2$), 3.81 (b, 6H, OCH$_3$), 3.66 (b, 4H, CH$_2$), 3.48 (b, 4H, CH$_2$). $^{13}$C-NMR (DMSO-d$_6$): δ 168.9, 163.3, 151.8, 148.6, 141.8, 133.4, 124.0, 123.1, 117.9, 113.2, 70.8, 70.3, 68.1, 59.8. IR (KBr, cm$^{-1}$): 1800-1710 (C═O, anhydride and ester region), 1630 and 1600 (C═C). M$_w$, =15,400 Da, PDI=1.4. T$_g$=49° C. T$_d$=251° C.

Relative Diacid (4) Hydrophobicity (Meng Q C, Zou H, Johansson J S, Eckenhoff R G, *Anal Biochem* 2001, 292, 102-6; OECD Nuclear Energy Agency., Organisation for Economic Co-operation and Development. Partition coefficient (1-octanol/water), High Performance Liquid Chromatography (HPLC) Method. Paris: Organisation for Economic Co-Operation and Development; 2004). A polymeric reverse-phase C$_{18}$ (RP18) column was used to measure the diacid hydrophobicity. Studies were performed on an XTerra® RP18 5 μm 4.6×150 mm column (Waters, Milford, Mass.) on a Waters 2695 Separations Module equipped with a Waters 2487 Dual λ, Absorbance Detector using a mobile phase consisting of 50 mM KH$_2$PO$_4$ with 1% formic acid in DI water at pH 2.5 (65%) and acetonitrile (35%) run at 1 mL/min flow rate at ambient temperature using λ=255 and 275 nm for reference samples and λ=320 nm for diacid samples. HPLC was carried out after all samples were filtered using 0.22 μm poly(vinylidine fluoride) syringe filters and subsequently injected (20 μL) using an autosampler. Samples were prepared in phosphate buffered saline (PBS). The phase preference is expressed by capacity factor k', where k' can be calculated using Equation 1, and t$_R$ and t$_0$ are the retention times of the sample and PBS, respectively.

$$k'=(t_R-t_0)/t_0 \quad \text{Equation 1}$$

$$\log P_{o,w}=\text{slope}*\log k'+y\text{-intercept} \quad \text{Equation 2}$$

Toluene, thymol, anisole, and benzyl alcohol were used as reference samples and their retention times obtained. A calibration curve was generated using published log P$_{o,w}$ values (OECD Nuclear Energy Agency., Organisation for Economic Co-operation and Development. Partition coefficient (1-octanol/water), High Performance Liquid Chromatography (HPLC) Method. Paris: Organisation for Economic Co-Operation and Development; 2004.) for the reference samples plotted on the y-axis and calculated log k' values for the x-axis. This curve was used to find the extrapolated log P diacid values of the regression line using Equation 2.

Contact Angle Measurements for Polymer.

Static contact angles were measured by dropping deionized water onto pressed polymer discs using a Ramé-Hart Standard Goniometer Model Number 250-00 156 (Mountain Lakes, N.J.) outfitted with a Dell Dimension 3000 computer with DROPimage Advanced software.

Polymer Swelling Measurements.

Triplicate samples of polymer discs were prepared by pressing ground polymer (50±5 mg) into 8 mm diameter×1 mm thick discs in an IR pellet die (International Crystal Laboratories, Garfield, N.J.) with a bench-top hydraulic press (Carver model M, Wabash, Ind.). Pressure of 10,000 psi was applied for 10 min at room temperature. All weights were measured gravimetrically. The dry weights were measured by subtracting the vial weight from the weight of the vial with polymer. Samples were submerged in 10 mL PBS. Media was removed at regular time intervals using a pipet before weighing the polymer inside the vial (wet weight) and subsequently drying under vacuum for 24 hours. Swelling was calculated according to Equation 3 where w$_w$ is wet weight and w$_d$ is dry weight.

$$[(W_w-w_d)/w_d]*100 \quad \text{Equation 3}$$

In Vitro FA Release.

Polymer degradation was measured as a function of FA release. Triplicate samples of polymer discs were prepared by pressing ground polymer (50±5 mg) into 8 mm diameter×1 mm thick discs in an IR pellet die (International Crystal Laboratories, Garfield, N.J.) with a bench-top hydraulic press (Carver model M, Wabash, Ind.). Pressure of 10,000 psi was applied for 10 min at room temperature. This methodology was preferred as it minimized interferences from external effects (e.g., formulation additives) on polymer degradation. The PBS pH was adjusted to 7.40 using 1 N sodium hydroxide. All pH measurements were performed using an Accumet® AR15 pH meter (Fisher Scientific, Fair Lawn, N.J.).

FA release was monitored by placing polymer discs into 20 mL Wheaton glass scintillation vials with 10 mL of PBS and incubated at 37° C. with agitation at 60 rpm using a controlled environment incubator-shaker (New Brunswick Scientific Co., Edison, N.J.). Media was collected every 24 hours for 20 days and replaced with fresh PBS (10 mL). Spent media was analyzed via high-performance liquid chromatography (HPLC). The degradation products were analyzed and quantified via HPLC using an XTerra® RP18 5 μm 4.6×150 mm column (Waters, Milford, Mass.) on a Waters 2695 Separations Module equipped with a Waters 2487 Dual A. Absorbance Detector. All samples were filtered using 0.22 μm poly(vinylidine fluoride) syringe filters and subsequently injected (20 μL) using an autosampler. The mobile phase was comprised of 50 mM KH$_2$PO$_4$ with 1% formic acid in DI water at pH 2.5 (65%) and acetonitrile (35%) run at 1 mL/min flow rate at ambient temperature. Absorbance was monitored at λ=320 nm. Amounts were calculated from known concentrations of standard FA solutions.

Antioxidant Activity.

The degradation antioxidant activity was assessed and compared to free ferulic acid using a 2,2-diphenyl-1-picrylhydrazyl (DPPH) radical scavenging assay. Antioxidant activity was evaluated by adding sample (0.1 mL) to a 0.024 mg/mL DPPH solution in methanol (3.9 mL). Day-10 samples (0.1 mL) from the each polymer degradation media were mixed with the 0.024 mg/mL DPPH solution (3.9 mL) at room temperature. After 1 hour, solutions were analyzed via UV/vis with a Perkin-Elmer Lambda XLS spectrophotometer (Waltham, Mass.) (λ=517 nm). Fresh FA solutions prepared at specific concentrations corresponding to day-10 HPLC data were each analyzed identically to the aforementioned degradation media samples. DPPH % radical reduction was calculated by: $[(Abs_{r0}-Abs_t)/Abs_{r0}]\times 100$, where $Abs_{r0}$ is the initial absorbance and $Abs_t$ is the absorbance after 1 hour. Absorbance values from adding PBS (0.1 mL) to the DPPH solution (3.9 mL) was used as $Abs_{r0}$. All radical scavenging assays were performed in triplicate. Student's t-tests were performed to determine significant differences between free FA and FA degradation media antioxidant activity ($p<0.05$).

Results and Discussion

Synthesis and Characterization.

Figure 2:
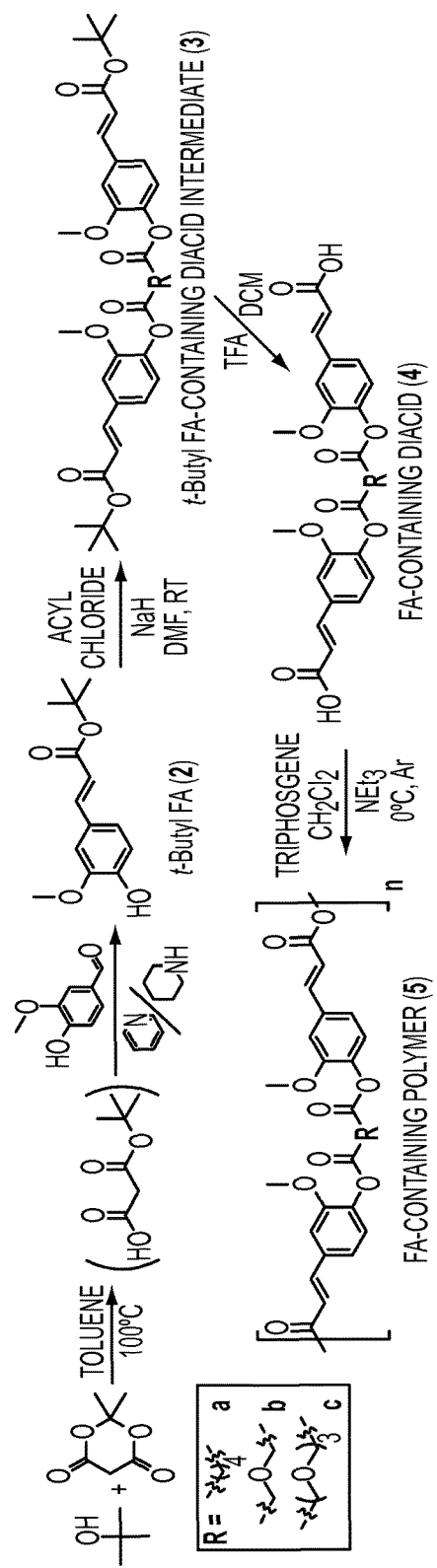
FIG. 2. Synthesis of ferulic acid-containing poly(anhydride-esters) (5) and FA-containing polymer precursors including diacids (4) and t-butyl intermediates (3) with varying linkers (a (Ouimet, *Biomacromolecules* 2013, 14, 854-61), b, c). Polymers, precursors and intermediates with comprising other bioactives described herein, such as coumaric acid or sinapic acid, may be similarly synthesized. Additionally, polymers, precursors and intermediates with comprising other linker molecules described herein may also be similarly synthesized.
Figure 3:
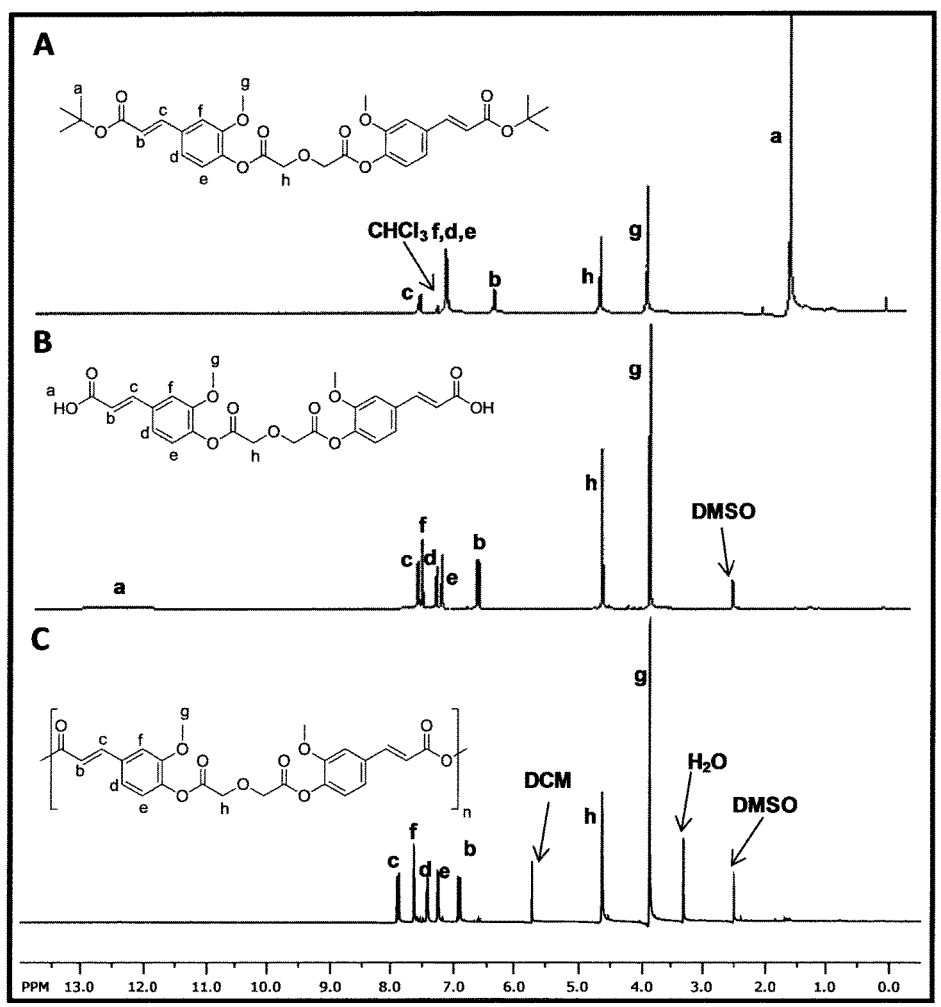
FIG. 3. $^1$H NMR spectra of ferulic acid (diglycolic) polymer and each intermediate step. t-butyl ferulic acid (diglycolic) intermediate 3b (A), ferulic acid (diglycolic) 4b (B), and ferulic acid (diglycolic) polymer, 5b (C) spectra are illustrated above.
Figure 4:
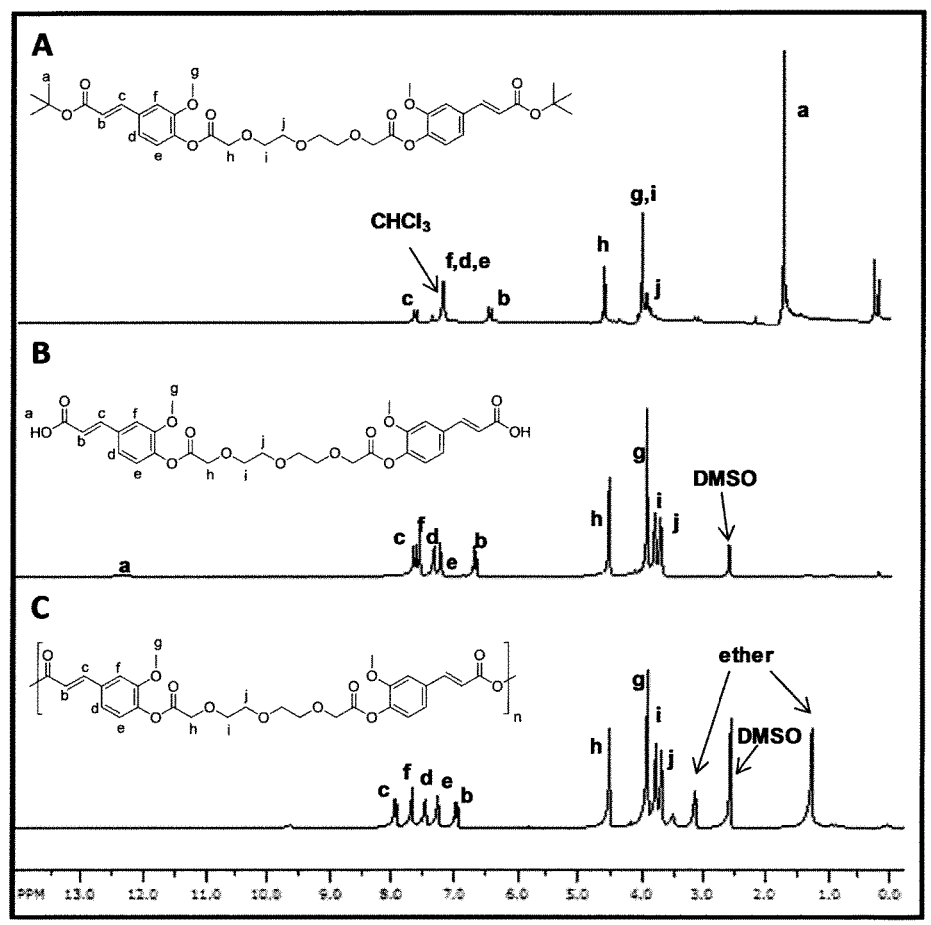
FIG. 4. $^1$H NMR spectra of ferulic acid (tetraglycolic) polymer and each intermediate step. t-butyl ferulic acid (tetraglycolic) intermediate 3c (A), ferulic acid (tetraglycolic) 4c (B), and ferulic acid (tetraglycolic) polymer, 5c (C) spectra are illustrated above.

Polymers were successfully prepared by chemically incorporating ferulic acid into the backbone via ester and anhydride bonds. The commercial availability of diglycolyl chloride was beneficial, which was not the case for tetraglycolyl chloride. Tetraglycolic acid, which was commercially available, was acylated using thionyl chloride to obtain a dichlorinated molecule. The acyl chloride (both tetraglycolic and diglycolic) were each separately reacted with t-butyl ferulic acid to yield 3 (FIGS. 2, 3A and 4A), and subsequently deprotected using TFA, denoted by the t-butyl group disappearance at 1.54 ppm. The synthesized diacid (4, FIGS. 2, 3B and 4B) underwent solution polymerization using triphosgene as a coupling agent to yield polymer (FIGS. 2, 3C and 4C). A successful synthesis of each step was fully characterized.

Polymer properties' results are listed in Table 1. Polymers were obtained in $M_w$ values ranging from 15,400-21,700 Da with 1.3-1.7 PDI values. Ferulic acid loading was modified using the different linker structures; as linker mass increased, ferulic acid chemically incorporated in the polymer backbone decreased giving a 5a>5b>5c drug loading trend. Glass transition and decomposition temperatures decreased with increasing linker chain length due to the enhanced flexibility. The trend in linker chain length observed was 5b>5a>5c. For example, due to the greatest linker chain length and thus enhanced flexibility, 5c exhibited the lowest $T_g$ value ($T_g$=49° C.). Similarly, 5a exhibited a Tg value lower than 5b ($T_g$ 5a=82° C. (Ouimet et al., *Biomacromolecules* 2013, 14, 854-61), $T_g$ 5 b=108° C.).

TABLE 1

Polymer characterization including drug loading percentage, $M_w$, PDI, $T_g$, $T_d$, and contact angle measurements.

| | Drug loading (%) | $M_w$ (Da) | PDI | $T_g$ (° C.) | $T_d$ (° C.) | Contact angle (degrees) |
|---|---|---|---|---|---|---|
| 5a[10] | 81 | 21,700 | 1.7 | 82 | 332 | 52 |
| 5b | 79 | 18,300 | 1.3 | 108 | 338 | 34 |
| 5c | 67 | 15,400 | 1.4 | 49 | 251 | 17 |

Relative Diacid (4) Hydrophobicity.

Measuring the diacid (4) water solubility proved difficult as diacid quickly degraded into ferulic acid. Therefore, a log P extrapolation method via HPLC was used. Capacity factor, k', values were calculated by Equation 1 after the diacid retention times were obtained using HPLC (Table 2). Although not a direct correlation with solubility limits, the log P value indicates whether a compound is more or less soluble in water versus oil. With this, a lower log P value correlates to an increase in hydrophilicity. The calculated log P values in Table 2 demonstrate a trend where 4a hydrophilicity<4b<4c.

TABLE 2

Calculated log P values for diacid molecules to elucidate their hydrophobicity

| Sample | Retention time (min) | Calculated log P values |
|---|---|---|
| 7.4a | 19.19 | 2.2 |
| 7.4b | 15.35 | 2.0 |
| 7.4c | 12.92 | 1.8 |

Contact Angle Measurements.

To evaluate relative hydrophilicity, static contact angles were measured by dropping deionized water onto a pressed polymer disc surface as a factor that may influence ferulic acid release rates. The polymers were found to be relatively hydrophobic with contact angles ranging from 52-17 degrees (Table 1). As oxygen content increased, relative hydrophilicity increased as indicated by the decrease in contact angle, which is in accordance with other published glycol-containing polyanhydrides (Hou et al., *Macromol Biosci* 2007, 7, 620-8). During measurements, the water droplet gradually expanded on the pressed polymer 5c disc, whereas the water droplets for 5a and 5b remained stagnant, further indicating increased hydrophilicity as glycol functionality increased. Relative hydrophilicity may influence the degradation rate and subsequent bioactive release, as water penetration into the polymeric matrix is an important factor in degradation of polyanhydrides (Göpferich A, Tessmar J, *Adv Drug Deliv Rev* 2002, 54, 911-31; Gopferich A, *Biomaterials* 1996, 17, 103-14). Polymer 5a exhibited the lowest contact angle value and also displayed the fasted release rates relative to polymers 5b and 5c.

Polymer Swelling Measurements.

Polymer swelling was obtained by subtracting polymer wet weight from the dry weight and dividing by dry weight on a particular day. Differences in swelling values are due to increased hydrophilicity from the additional ethylene oxide groups. Extensive bulk erosion was presumably taking place as confirmed by the loss of structural integrity around day 6 for 5c. Swelling acts as a mechanism by which polymer degradation within inner layers of polymer matrix is activated thus enabling both surface and bulk erosion.

In Vitro Ferulic Acid Release.

Figure 5:
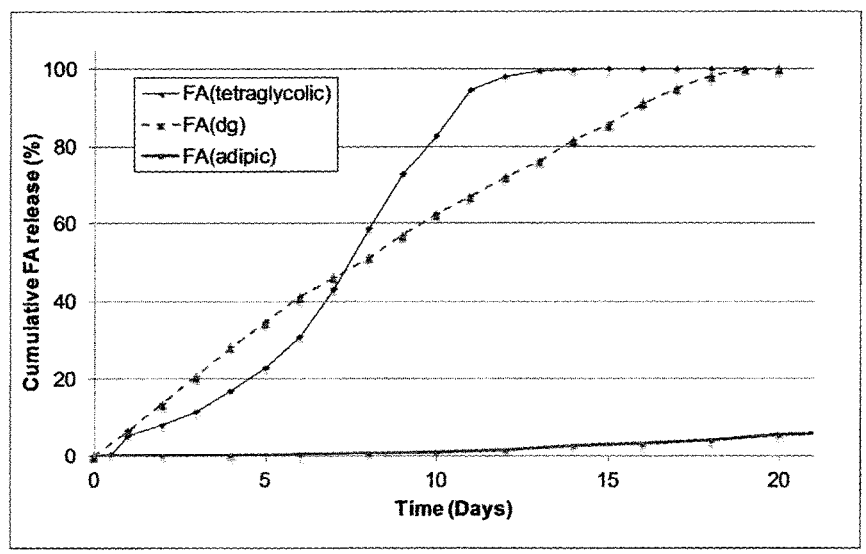
FIG. 5. Percent cumulative ferulic acid (FA) release over time for ferulic acid (adipic) polymer (5a), ferulic acid (diglycolic) polymer (5b), and ferulic acid (tetraglycolic) polymer (5c).

Polymer degradation was measured by quantifying ferulic acid in degradation media measured by HPLC as its appearance is indicative of both anhydride and ester bond hydrolysis (see, FIG. 5). Discs were used to enable uniform polymer degradation, without additional formulation steps, which may alter degradation and thus ferulic acid release. Relative hydrolysis rates of the hydrolytically labile bonds was not apparent as diacid absorbance ($R_t$=15.35 and 12.92 min for 4b and 4c, respectively) was minimal at the observed wavelengths. Additionally, diacid solubility in PBS varied with glycol content. Detection of 1 ($R_t$=2.98 min) indicated complete ester and anhydride bond hydrolysis with no decomposition peaks observed.

Figure 6:
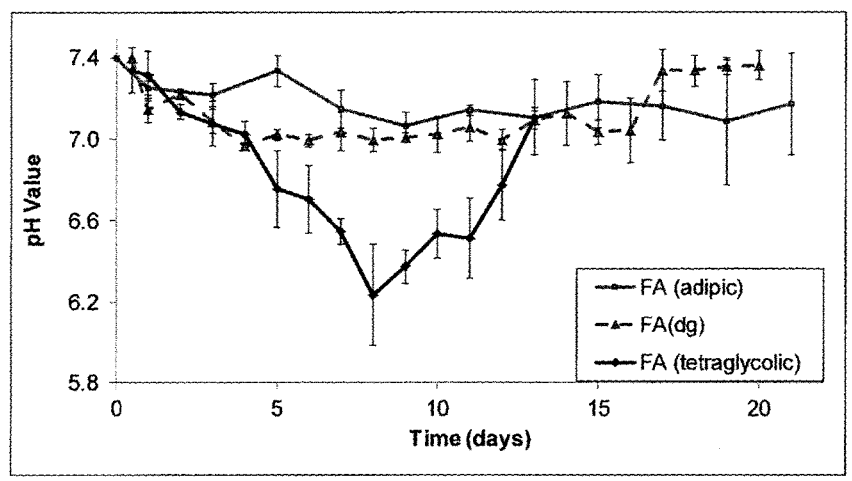
FIG. 6. Change of degradation media pH over time during in vitro studies.

The degradation media pH was monitored throughout the in vitro release tests. During polymer degradation, pH was always less than the initial pH=7.4 (FIG. 6). An initial state of swelling is observed for the FA (tetraglycolic) samples. Swelling is referred to as imbibing water by a polymer system, resulting in an increase in volume (Siegel R A, Rathbone M J. Overview of Controlled Release Mechanisms. In: Siegel R A, Rathbone M J, Siepmann J, editors. Fundamentals and Applications of Controlled Release Drug Delivery. New York: Springer; 2012. pp. 19-43). Water enters the polymer relatively rapidly due to ethylene oxide groups' ability to hydrogen bond and attracts water.

Initial slower ferulic acid release observed for polymer 5c is presumably due to initial water uptake and subsequent polymer degradation resulting in decreased intra-polymer pH, causing a pH gradient between the discs' surface and interior. Such a gradient presumably caused swelling to continue until a critical osmotic pressure was attained within the disc, at which point the degradation products were released. Once the degradation products were released from the disc, a larger internal surface area was available for erosion to occur, thus leading to an increased release rate. Difference in release rates (measured by slope of line) was attributed to the increased hydrophilicity due to the addition of ethylene glycol derivatives into the polymer backbone; release rates increased with 5c>5b>5a (8.02, 5.16, 0.29 for 5c, 5b, and 5a, respectively).

Antioxidant Assay.

Figure 7:
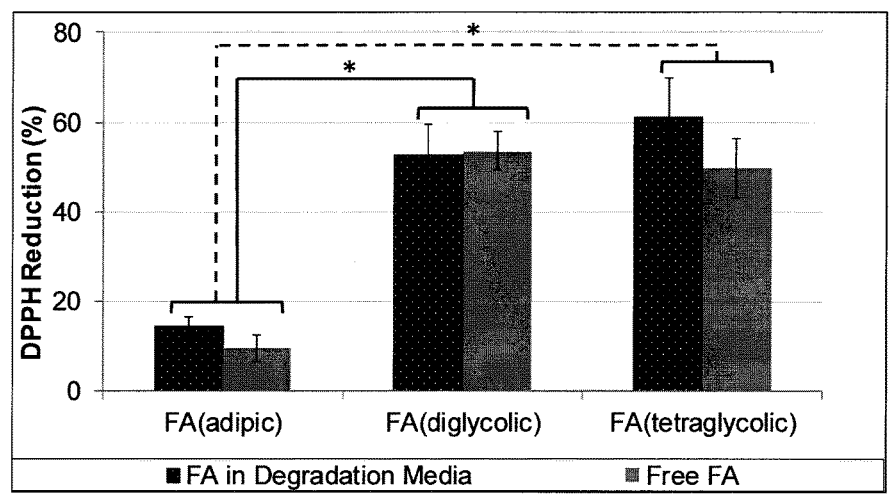
FIG. 7. Percent DPPH reduction for the ferulic acid (adipic) polymer (5a), ferulic acid (diglycolic) polymer (5b), and ferulic acid (tetraglycolic) polymer (5c) as compared to free ferulic acid (control).

A radical quenching assay was used to determine polymer degradation media antioxidant activity to ensure synthetic methods and release conditions did not influence ferulic acid activity (see, FIG. 7). The DPPH reduction percentage was expected to increase with increasing antioxidant activity, which is directly correlated to antioxidant concentration.

Conclusion

Compounds with antioxidant activity such as ferulic acid exhibit beneficial therapeutic properties to combat oxidative stress, but need better delivery. Such drug delivery systems are finding significant and diverse applications ranging from biomaterials to consumer products. Our approach is to incorporate glycol groups into the main chain of the polymer via chemical incorporation to tune the drug release rate and alter polymer properties was successful. Increasing the hydrophilicity enhances the ability to not only tune ferulic acid release depending on intended application, but also alter physicochemical properties. These biodegradable polymers can be beneficial for short-term drug delivery systems with an emphasis on utilizing glycol functionality to tailor antioxidant-based polymer physicochemical properties and release profiles.

Example 2

Ferulic Acid Polymer Microspheres.

Oxidative stress causes DNA damage leading to many debilitating diseases. As described herein, a ferulic acid-based polymer that degrades within three weeks was designed and synthesized. As the polymer degrades in the presence of water, ferulic acid is released. Ferulic acid is a potent antioxidant with radical scavenging and photoprotective properties useful to combat oxidative stress and therefore used in cosmetics as a topical antioxidant in anti-aging remedies and sunscreens.

Several delivery systems employed in cosmetics and personal care that utilize entrapment or adsorption technologies include emulsions, vesicles such as liposomes and hollow microparticles (empty with no drug), and suspensions. One of the most common methods to topically deliver bioactives is through suspensions and emulsions. Micromulsions can be utilized to directly entrap actives, fragrances, or flavors as bulk emulsions have been primary formulations in the cosmetic industry. These microspheres are advantageous over using a disc in that the surface area is greatly increased, thus accelerating bioactive release. Furthermore, these microspheres can act as carriers to encapsulate other bioactive molecules for dual release and potential synergistic activity.

Accordingly, ferulic acid (FA)-containing polymers with a diglycolic linker were formulated into microspheres and subsequently characterized. Other polymers described herein (e.g., comprising a different bioactive or linker) may also be formulated into microspheres using similar methods as those described below.

Materials and Methods

Microsphere Preparation.

Ferulic acid (FA)-containing polymer using a diglycolic linker was synthesized according to Example 1 and was formulated into microspheres using an oil-in-water single emulsion solvent evaporation technique (Yeagy, *J Microencapsulation* 2006, 23, 643-53). In general, FA-containing polymer (0.50 g) was dissolved in dichloromethane (3 mL) and added drop-wise to 1% aqueous poly(vinyl alcohol) (PVA) solution (80 mL) at room temperature. The emulsion was homogenized for 2 min using an IKA Ultra-Turrax T8 homogenizer at approximately 10,000 rpm. The homogenized solution was left stirring for 2 h to allow microsphere formation by solvent evaporation. Microspheres were transferred to sterile 50 mL polypropylene conical tubes, washed with acidic water (pH 1) to remove residual PVA, centrifuged at 3,000 rpm for 10 min and supernatant decanted. This was repeated 5 times. Microspheres were frozen by placing the conical tubes in a dry ice/acetone bath and lyophilized for 24 h at −40° C. and 133×10-3 mBar (LABCONO Freeze Dry System/Freezon 4.5).

Size and Morphology.

Size and morphology of the microspheres were determined using SEM. Images for each set of microspheres were obtained using an AMRAY-1830I microscope (AMRAY Inc.) after coating the samples with Au/Pd using a sputter coater (SCD 004, Blazers Union Limited). SEM images of each polymer microsphere sample were then analyzed using NIH ImageJ software. Distributions of particle diameter were obtained by evaluating>50 particles per sample.

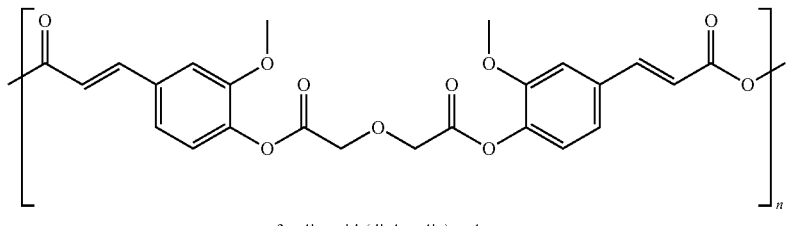

ferulic acid (diglycolic) polymer

Molecular Weight.

Polymer precursors were analyzed via mass spectrometry to determine molecular weights. A Finnigan LCQ-DUO equipped with Xcalibur software and an adjustable atmospheric pressure ionization electrospray ion source (API-ESI Ion Source) was used with a pressure of $0.8 \times 10^{-5}$ and 150° C. API temperature. Samples dissolved in methanol (<10 µg/mL) were injected with a glass syringe. GPC was used to determine polymer weight-averaged molecular weight and polydispersity using a Perkin-Elmer liquid chromatography system consisting of a Series 200 refractive index detector, a Series 200 LC pump, and an ISS 200 autosampler. Automation of the samples and processing of the data was performed using a Dell OptiPlex GX110 computer running Perkin-Elmer TurboChrom 4 software with a Perkin-Elmer Nelson 900 Series Interface and 600 Series Link. Polymer samples were prepared for autoinjection by dissolving in dichloromethane (DCM, 10 mg/mL) and filtering through 0.45 µm poly(tetrafluoroethylene) syringe filters. Samples were resolved on a Jordi divinylbenzene mixed-bed GPC column (7.8×300 mm, Alltech Associates, Deerfield, Ill.) at 25° C., with DCM as the mobile phase at a flow rate of 1.0 mL/min. Molecular weights were calibrated relative to broad polystyrene standards (Polymer Source Inc., Dorval, Canada).

Thermal Properties.

DSC measurements were carried out on TA Instrument Q200 to determine melting ($T_m$) and glass transition ($T_g$) temperatures. Measurements on samples (4-6 mg) heated under nitrogen atmosphere from −10° C. to 200° C. at a heating rate of 10° C./min and cooled to −10° C. at a rate of 10° C./min with a two-cycle minimum were performed. TA Instruments Universal Analysis 2000 software, version 4.5A was used to analyze the data. TGA was utilized for determining decomposition temperatures ($T_d$) using a Perkin-Elmer Pyris 1 system with TAC 7/DX instrument controller and Perkin-Elmer Pyris software for data collection. Samples (5-10 mg) were heated under nitrogen atmosphere from 25° C. to 400° C. at a heating rate of 10° C./min. Decomposition temperatures were measured at the onset of thermal decomposition.

In Vitro Ferulic Acid Release.

FA release from polymer microspheres was studied at 37° C. in phosphate buffered saline (PBS) at pH 7.4 with agitation (60 rpm) to mimic physiological conditions. Triplicate samples of microspheres (20.0 mg) were suspended in 20 mL of PBS. After 12 hours, and every 24 hours after day 1, samples were centrifuged at 3,000 rpm for 5 minutes (Hettich Zentrifugen EBA12) to allow microspheres to settle to the bottom. Aliquots of the supernatant (15 mL) were collected and replaced with fresh PBS (15 mL). Spent media was analyzed via high-performance liquid chromatography (HPLC). The degradation products were analyzed and quantified via HPLC using an XTerra® RP18 5 µm 4.6×150 mm column (Waters, Milford, Mass.) on a Waters 2695 Separations Module equipped with a Waters 2487 Dual λ Absorbance Detector. All samples were filtered using 0.22 µm poly(vinylidine fluoride) syringe filters and subsequently injected (20 µL) using an autosampler. The mobile phase was comprised of 50 mM $KH_2PO_4$ with 1% formic acid in DI water at pH 2.5 (65%) and acetonitrile (35%) run at 1 mL/min flow rate at ambient temperature. Absorbance was monitored at λ=320 nm. Amounts were calculated from known concentrations of standard FA solutions.

Results and Discussion

The microsphere $M_w$ and $T_g$ were determined and compared to the values obtained for the unprocessed polymers (Table 3). A slight Mw decrease and increase in PDI compared to the unprocessed polymer was observed as expected due to the water exposure during formulation. The changes in $T_g$ values decreased post formulation, but maintained above 37° C., which ensure their shape will remain if used in vivo.

TABLE 3

Molecular weight, MW (polymer and microspheres), glass transition temperature, Tg (polymer and microspheres), and % yield (microspheres).

| | Mw (Da) Polymer (PDI) | Mw (Da) Microspheres | Tg (C.) polymer | Tg (° C.) microspheres | % Yield microspheres |
|---|---|---|---|---|---|
| Polymer | 18,300 (1.3) | 15,500 (1.5) | 108 | 80 | 83 |

Figure 8:
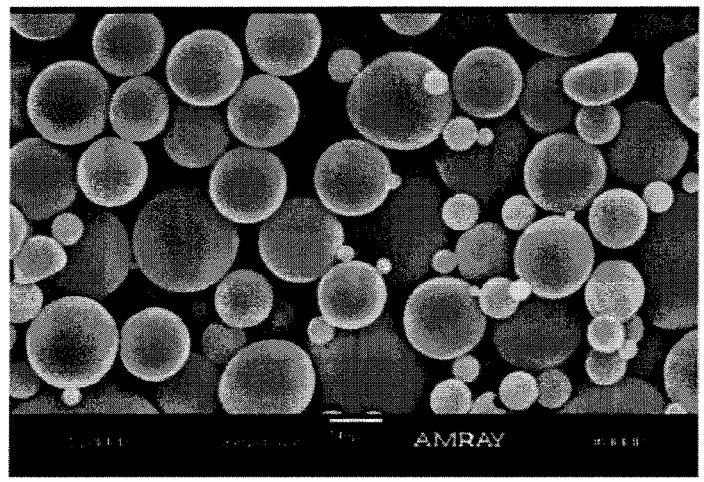
FIG. 8. (A) Representative scanning electron microscopy images of microspheres prepared from the FA-containing polymer with a diglycolic linker. (B) In vitro ferulic acid release from polymer microspheres (diglycolic linker) (FA±standard deviation).
Figure 8:
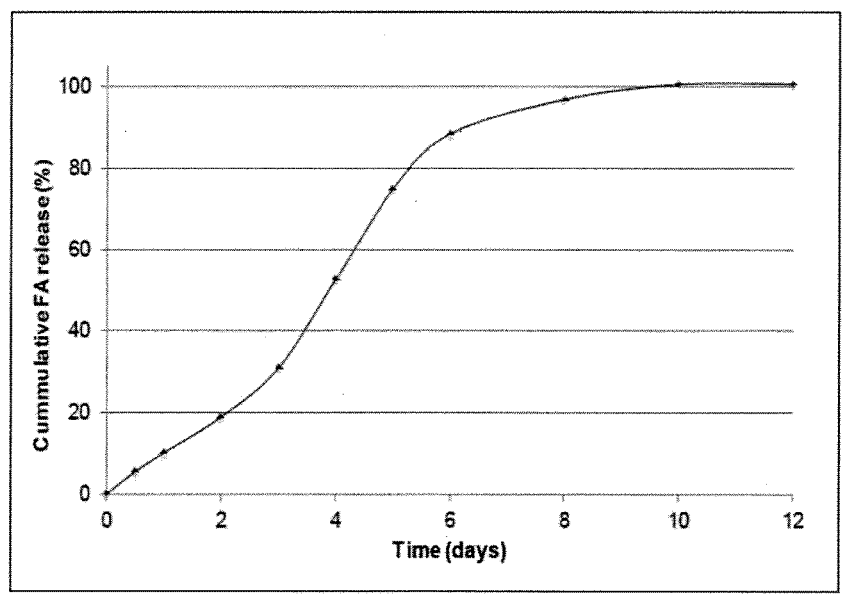

Microspheres 2-27 µm in diameter were obtained in 83% yield without aggregation and are represented in FIG. 8A. Smooth microsphere surfaces are important for uniform bioactive release. Additionally, size distribution, homogenization speed and polymer concentration may be varied.

The polymer microsphere's in vitro degradation was measured by the appearance of ferulic acid release in degradation media via HPLC. FA detection with a 3.71 minute retention time indicated complete of anhydride and ester bond hydrolysis. The polymer microspheres released 100% ferulic acid over 10 days compared to polymer discs, which took 20 days for total release (see, FIG. 8B).

The invention described herein also comprises compositions, devices, methods of use and methods of treatment which are disclosed herein, e.g., in Example 1 and Example 2.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:
1. A polymer selected from:

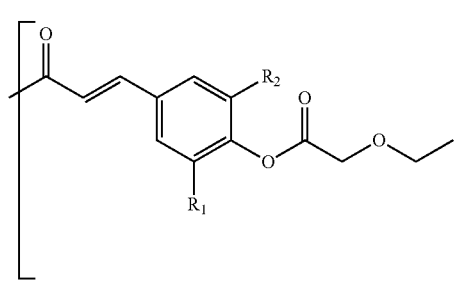

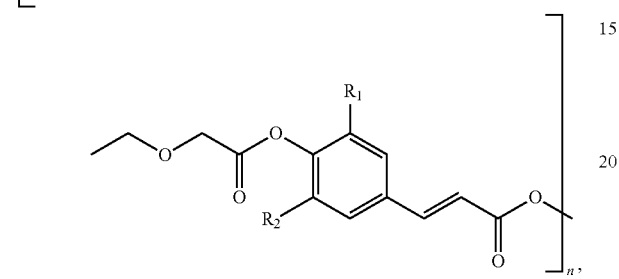

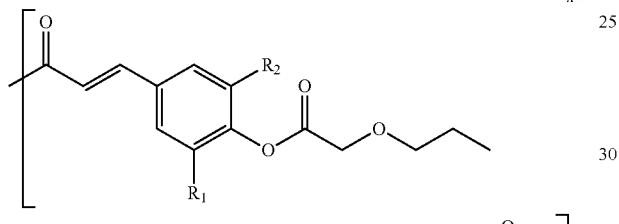

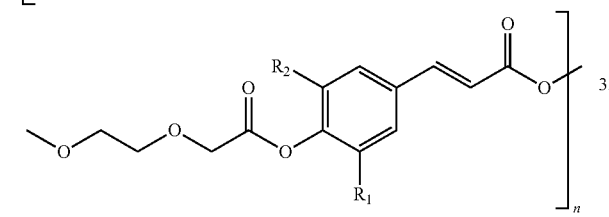

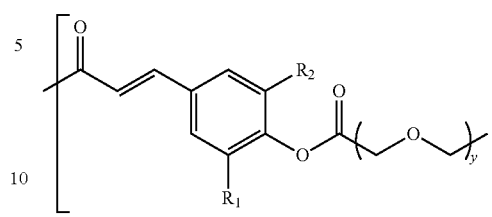

and

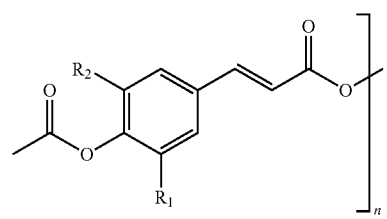

wherein $R_1$ is $OCH_3$ and $R_2$ is H; $R_1$ is $OCH_3$ and $R_2$ is $OCH_3$; or $R_1$ is H and $R_2$ is H;

wherein y is 4 or more;

and wherein n is 2 or more.

2. The polymer of claim 1, wherein $R_1$ is $OCH_3$ and $R_2$ is H.

3. The polymer of claim 1, wherein $R_1$ is $OCH_3$ and $R_2$ is $OCH_3$.

4. The polymer of claim 1, wherein $R_1$ is H and $R_2$ is H.

5. A microsphere comprising the polymer as described in claim 1.

6. A diacid selected from:

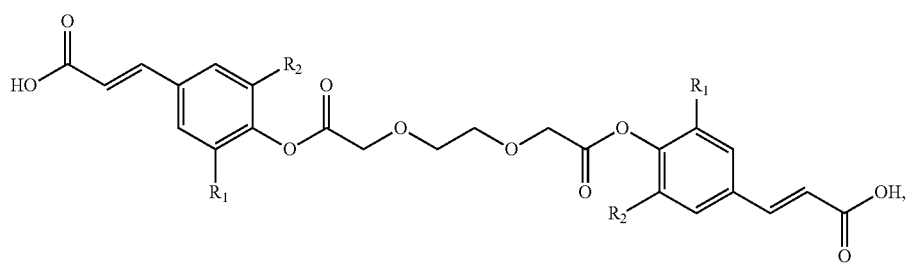

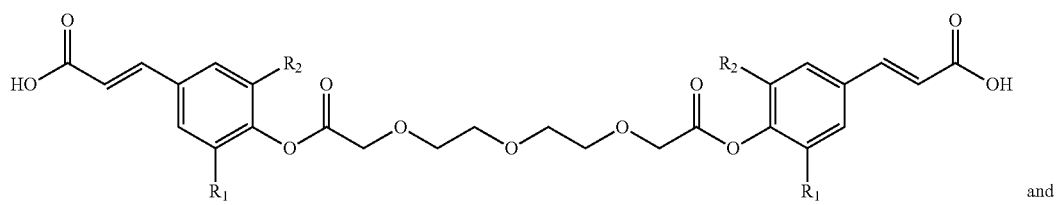

and

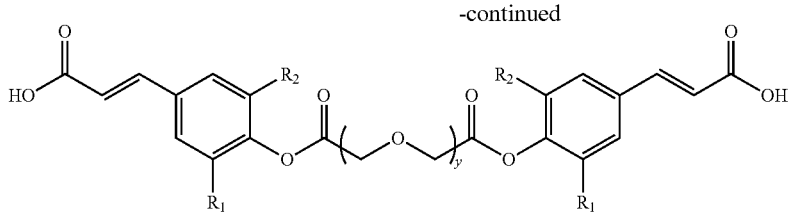

wherein $R_1$ is $OCH_3$ and $R_2$ is H; $R_1$ is $OCH_3$ and $R_2$ is $OCH_3$; or $R_1$ is H and $R_2$ is H; and wherein y is 4 or more.

7. A pharmaceutical composition comprising the polymer as described in claim 1 and a pharmaceutically acceptable carrier.

8. A cosmetic comprising the polymer as described in claim 1.

9. A sunscreen comprising the polymer as described in claim 1.

10. A method of reducing oxidative stress in a cell of a mammal, preventing photodamage in skin of a mammal, and/or treating a disorder associated with oxidative stress in a mammal, comprising administering the polymer as described in claim 1 to the mammal.

11. The method of claim 10, wherein the polymer is administered topically.

12. A hydrogel comprising a blend comprising (a) the polymer as described in claim 1 and (b) a hydrophilic polymer.

13. The hydrogel of claim 12, wherein the hydrophilic polymer is selected from the group consisting of poly(N-vinyl-2-pyrrolidone), poly(vinyl alcohol), and poly(ethylene oxide).

14. The hydrogel of claim 13, wherein the hydrophilic polymer is poly(N-vinyl-2-pyrrolidone).

15. The hydrogel of claim 12, wherein the polymer as described in claim 1 is physically crosslinked with the hydrophilic polymer through hydrophobic interactions.

16. A method of making a hydrogel comprising blending and solvent casting (a) the polymer as described in claim 1 and (b) a hydrophilic polymer, under conditions that provide a hydrogel.

17. The method of claim 16, further comprising crosslinking (a) the polymer as described in claim 1 with (b) the hydrophilic polymer, wherein the crosslinking is by ultraviolet radiation, gamma radiation, or a crosslinking agent.

18. A method for promoting wound healing in a mammal, comprising contacting the hydrogel as described in claim 12 with a wound of the mammal.

19. A method of therapeutically treating the skin of a mammal, comprising contacting the hydrogel as described in claim 12 with the skin of the mammal.

* * * * *